US012217855B1

(12) United States Patent
Douglas et al.

(10) Patent No.: US 12,217,855 B1
(45) Date of Patent: *Feb. 4, 2025

(54) METHOD AND APPARATUS FOR ALTERING 3D DATASETS

(71) Applicants: Robert Edwin Douglas, Winter Park, FL (US); David Byron Douglas, Winter Park, FL (US)

(72) Inventors: Robert Edwin Douglas, Winter Park, FL (US); David Byron Douglas, Winter Park, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/369,146

(22) Filed: Sep. 16, 2023

Related U.S. Application Data

(63) Continuation of application No. 17/485,632, filed on Sep. 27, 2021, now Pat. No. 11,763,934, which is a continuation-in-part of application No. 17/169,483, filed on Feb. 7, 2021, now Pat. No. 11,183,296, and a continuation-in-part of application No. 16/951,813, filed on Nov. 18, 2020, now Pat. No. 11,295,537, and a continuation-in-part of application No. 17/093,322, filed on Nov. 9, 2020, now Pat. No. 11,395,701, and a continuation-in-part of application No. 16/867,102, filed on May 5, 2020, now Pat. No. 11,210,867, said application No. 17/169,483 is a continuation of application No. 16/736,731, filed on Jan. 7, 2020, now Pat. No. 10,950,338, which is a continuation-in-part of application No. 16/195,251, filed on Nov. 19, 2018, now Pat. No. 10,878,639, said application No. 17/093,322 is a continuation of application No. 16/010,925, filed on Jun. 18, 2018, now Pat. No. 10,864,043, said application No. 16/195,251 is a continuation-in-part of application (Continued)

(51) Int. Cl.
*G16H 30/40* (2018.01)
*G06F 30/27* (2020.01)
*G06N 20/00* (2019.01)
*G06T 15/08* (2011.01)
*G06T 17/10* (2006.01)
*G06T 19/20* (2011.01)
*G09B 9/00* (2006.01)

(52) U.S. Cl.
CPC ............. *G16H 30/40* (2018.01); *G06F 30/27* (2020.01); *G06N 20/00* (2019.01); *G06T 15/08* (2013.01); *G06T 17/10* (2013.01); *G06T 19/20* (2013.01); *G09B 9/00* (2013.01); *G06T 2210/41* (2013.01)

(58) Field of Classification Search
None
See application file for complete search history.

(56) References Cited

U.S. PATENT DOCUMENTS 11,183,296 B1 * 11/2021 Douglas .................. G16H 30/20
11,763,934 B1 * 9/2023 Douglas .................. A61B 34/10
345/419

(Continued)

*Primary Examiner* — James A Thompson

(57) ABSTRACT

A method and apparatus for performing a simulation of a change of a three-dimensional dataset of a physical item is disclosed. Voxels within the three-dimensional dataset are modified to mimic the change. Some embodiments comprise using artificial intelligence algorithm to determine the change. Simulations can be performed over multiple time points.

20 Claims, 24 Drawing Sheets

Related U.S. Application Data

No. 15/904,092, filed on Feb. 23, 2018, now Pat. No. 10,586,400.

(60) Provisional application No. 62/843,612, filed on May 6, 2019, provisional application No. 62/695,868, filed on Jul. 10, 2018, provisional application No. 62/651,934, filed on Apr. 3, 2018, provisional application No. 62/628,527, filed on Feb. 9, 2018.

(56) References Cited

U.S. PATENT DOCUMENTS

| | | | | |
|---|---|---|---|---|
| 2004/0207652 | A1* | 10/2004 | Ratti | G06V 10/10 345/697 |
| 2009/0322748 | A1* | 12/2009 | Chen | G06T 7/11 345/424 |
| 2013/0230224 | A1* | 9/2013 | Claude | G06T 7/12 382/173 |
| 2019/0057555 | A1* | 2/2019 | Gallop | G06T 19/20 |
| 2020/0085396 | A1* | 3/2020 | Song | A61B 5/7278 |

* cited by examiner

METHOD AND APPARATUS FOR ALTERING 3D DATASETS

CROSS REFERENCE TO RELATED APPLICATIONS

The present application is a continuation of Ser. No. 17/485,632 filed on Sep. 27, 2021, which is a CIP of Ser. No. 17/169,483 Feb. 7, 2021 U.S. Pat. No. 11,183,296, which is a CON of Ser. No. 16/736,731 Jan. 7, 2020 U.S. Pat. No. 10,950,338. U.S. patent application Ser. No. 17/485,632 is a CIP of Ser. No. 17/093,322 Nov. 9, 2020 U.S. Pat. No. 11,395,701, which is a CON of Ser. No. 16/010,925 Jun. 18, 2018 U.S. Pat. No. 10,864,043, which claims benefit of 62/628,527 Feb. 9, 2018. U.S. patent application Ser. No. 16/736,731 Jan. 7, 2020 is a CIP of Ser. No. 16/195,251 Nov. 19, 2018 U.S. Pat. No. 10,878,639, which is a CIP of Ser. No. 15/904,092 Feb. 23, 2018 U.S. Pat. No. 10,586,400, and claims benefit of 62/695,868 Jul. 10, 2018, and claims benefit of 62/651,934 Apr. 3, 2018, and claims benefit of 62/628,527 Feb. 9, 2018. U.S. patent application Ser. No. 17/485,632 is a CIP of Ser. No. 16/951,813 Nov. 18, 2020 and is a CIP of Ser. No. 16/867,102 May 5, 2020 U.S. Pat. No. 11,210,867, which claims benefit of 62/843,612 May 6, 2019.

TECHNICAL FIELD

Aspects of this disclosure are generally related to radiological imaging, and more particularly to surgical planning.

BACKGROUND

One of the challenges that interventional radiologists and surgeons face prior to performing a surgery is selection of optimal hardware. Because of uncertainties, the surgeon may select several slightly different pieces of hardware for the same purpose, of which one piece may be optimal. Which piece of hardware is optimally suited to the purpose is determined during surgery.

SUMMARY

All examples, aspects and features mentioned in this document can be combined in any technically possible way.

In accordance with an aspect a method comprises: assigning tissue type properties to voxels of a medical image; and performing a three-dimensional simulation by manipulating the voxels based on the assigned tissue type properties and an input that prompts voxel manipulation. In some implementations assigning tissue type properties to the voxels of the medical image comprises assigning a value for at least one of: elasticity, ductility, hardness, density, and thermal conductivity. In some implementations manipulating the voxels comprises changing at least one of voxel size, voxel location, voxel orientation, voxel shape, voxel color, voxel grayscale, and voxel tissue type property value. In some implementations the input comprises inserting a virtual volume-subtending surgical object. In some implementations the input comprises inserting a virtual volume-subtending anatomic object. In some implementations performing the simulation comprises representing virtual motion. In some implementations performing the simulation comprises representing deformation of tissue. In some implementations performing the simulation comprises representing a radiological dissection. In some implementations performing the simulation comprises creating new voxels in response to the input. In some implementations creating new voxels comprises creating new fixed-type voxels that do not change unless acted upon by a user through an interface. In some implementations creating new voxels comprises creating new invisible-type voxels. In some implementations creating new voxels comprises creating new tissue-type voxels. In some implementations creating new voxels comprises creating new dynamic-type voxels having at least one tissue type property that changes over time. In some implementations creating new voxels comprises creating new mobile voxels that travel through a virtual vascular structure. In some implementations performing the simulation comprises eliminating selected voxels in response to the input. Some implementations comprise eliminating tissue type voxels to simulate ablation. Some implementations comprise inserting strategic elimination points that designate a direction in which voxels are eliminated in discrete steps. Some implementations comprise inserting strategic non-elimination points that designate voxels that are preserved from elimination. Some implementations comprise assignment of a strategic deformation feature that designates a maximum shift for at least one voxel.

In accordance with an aspect an apparatus comprises: an IO device; and an image processor in communication with the IO device, the image processors comprising a program stored on computer-readable non-transitory media, the program comprising: instructions that assign tissue type properties to voxels of a medical image; and instructions that perform a three-dimensional simulation by manipulating the voxels based on the assigned tissue type properties and an input that prompts voxel manipulation. In some implementations the instructions that assign tissue type properties to voxels assign a value for at least one of: elasticity, ductility, hardness, density, and thermal conductivity. In some implementations the instructions that perform the three-dimensional simulation by manipulating the voxels change at least one of voxel size, voxel location, voxel orientation, voxel shape, voxel color, voxel grayscale, and voxel tissue type property value. In some implementations the input comprises insertion of a virtual volume-subtending surgical object. In some implementations the input comprises insertion of a virtual volume-subtending anatomic object. In some implementations the simulation comprises representing virtual motion. In some implementations the simulation comprises representing deformation of tissue. In some implementations the simulation comprises representing a radiological dissection. In some implementations the simulation comprises creation of new voxels in response to the input. In some implementations creation of new voxels comprises creation of new fixed-type voxels that do not change unless acted upon by a user through an interface. In some implementations creation of new voxels comprises creation of new invisible-type voxels. In some implementations creation of new voxels comprises creation of new tissue-type voxels. In some implementations creation of new voxels comprises creation of new dynamic-type voxels having at least one tissue type property that changes over time. In some implementations creation of new voxels comprises creation of new mobile voxels that travel through a virtual vascular structure. In some implementations the simulation comprises elimination of selected voxels in response to the input. In some implementations elimination of selected voxels comprises elimination of tissue type voxels to simulate ablation. Some implementations comprise strategic elimination points that designate a direction in which voxels are eliminated in discrete steps. Some implementations comprise strategic non-elimination points that designate voxels that are preserved from elimination. Some implementations comprise a strategic deformation feature that designates a maximum shift for at least one voxel.

In accordance with an aspect, a method comprises: using a 3D volumetric medical imaging dataset; performing anatomic segmentation of voxels in the volumetric medical imaging dataset into distinct tissue types; assigning tissue properties (mechanical properties such as elasticity, ductility, hardness or physical properties such as density or thermal conductivity) to each tissue type in the medical imaging dataset by a combination of properties acquired from the scanner and by lookup table; performing options for voxel manipulation (e.g., changing at least one voxel's size, location, orientation, shape, color/grayscale, or other voxel property); performing options for voxel creation (e.g., fixed-location voxel creation such as tissue-type or invisible-type voxel creation, dynamic voxel creation such as virtual contrast, or interactive voxel creation, such as a virtual occluder that can interact with other voxels in the 3D medical imaging); performing options for voxel elimination (e.g., eliminate and discard via volume-type elimination or surface-type elimination, cut and place voxels into a virtual specimen container bucket; perform new applications including virtual motion, deformable tissue, virtual radiological dissection, perform annotations or recording the interactive steps for replay.

In accordance with an aspect a method comprises: performing of manipulation of at least one of the original voxel parameters including, but not limited to, at least one of the following: change size (e.g., increase or decrease at least one dimension of at least one voxel); change shape (e.g., change from cube shaped voxel to cylindrical shaped voxel); change in position (i.e., the center coordinate of the voxel changes in the x-direction, y-direction, and/or z-direction); change in orientation (i.e., the orientation of the voxel changes in roll, pitch and/or yaw); or change in internal parameter (e.g., texture, tissue property, etc.). Thus, at least one voxel has a final voxel parameter that differs from the original voxel parameter.

In accordance with an aspect a method comprises: performing anatomic segmentation of voxels in the 3D imaging dataset, such that all voxels are assigned both a tissue type (e.g., skin, fat, bone, cerebrospinal fluid, etc.) and tissue properties (e.g., mechanical properties such as elasticity, ductility, hardness, physical properties such as density or thermal conductivity, etc.) by a combination of properties acquired from the scanner, tissue segmentation and by lookup table.

In accordance with an aspect a method comprises: creation of fixed-type voxels. This implementation includes the creation of invisible-type voxels in between two closely spaced structures, such that the structures can be separated from one another. Another implementation is the creation of tissue-type voxels to stretch a structure. Another implementation is the creation of a combination of invisible-type voxels and tissue-type voxels, such that structures can be pulled apart for the purposes of untangling and better visualization of complex structures (e.g., improve visualization of a cerebral arteriovenous malformation). Other fixed-type voxels include, but are not limited to, the following: surgical-device-type voxels; fluid-type voxels (e.g., water, blood, etc.); non-fluid-type voxels (e.g., kidney tissue, etc.); or, others. This implementation includes creation of annotation-type voxels, which are attached to the structure of interest, but serve to facilitate understanding or communication of a finding. An example is annotation of voxel counting metrics, such as the markup of curvilinear distance.

Note that when viewing with 3D and rotation is used, the annotations will rotate such that they are optimally viewed from each viewing perspective.

In accordance with an aspect a method comprises: creation of dynamic-type voxels. This implementation includes the creation of mobile voxels, which have the capability to move through tubular shaped vascular structures from one end to another (e.g., proximal to distal) to improve visualization. The manner in which the mobile voxels move through the tubular vascular structures can be in accordance with any flow patterns, such as laminar flow or plug flow.

In accordance with an aspect a method comprises: creation of interactive-type voxels. This implementation includes the creation of voxels, which have the capability to interact with any voxels or tissues within the dataset, such as placement of voxels to mimic a surgical clip and occlude the flow of virtual contrast along some portion of a tubular blood vessel. Another example is soft tissue voxels changing in relation to the placement of a virtual occluder type interactive voxels. Another example of an interactive-type voxel is the insertion of a strategic deformation voxel, which can be used to guide the deformation of soft tissue voxels when a virtual surgical object is being inserted.

In accordance with an aspect a method comprises elimination of voxels in either a eliminate and discard approach (e.g., volumetric-type elimination, multi-step layer-by-layer ablative-type approach or elimination associated with the placement of a virtual object, cardinal direction-type elimination). One element to aid in the elimination of the desired voxels is through the use of strategic elimination points and strategic non-elimination points. Some implementations use a 3D cursor to eliminate voxels outside of the cursor. Some implementations use an ablative approach to take the form of elimination of the outer voxels from the whole surface, one voxel layer at a time. Other implementations with an ablative approach can take the form of elimination of the outer voxels from a portion of the whole surface, one voxel layer at a time. Other types include the elimination in accordance with placement of a virtual object.

In accordance with an aspect a method comprises: performing a coordinated multi-voxel manipulation to simulate motion of anatomical structures in accordance with the intrinsic properties (e.g., hardness, elasticity, etc.) of the voxels composing the anatomic structure. Two examples were provided in this patent for illustrative purposes. The first example is virtual motion at the knee joint. The second example is the movement of a virtual catheter inside a blood vessel, with an additional viewing option to include a tunnel view (as if the viewpoint was just short of the catheter tip and viewing both the catheter tip and the branches.

In accordance with an aspect, a method comprises: assignment of strategic deformation points (e.g., the user can specify which voxels are more or less deformable than predicted by the algorithm based on his/her prior knowledge to guide the coordinated multi-voxel shift to achieve the desired deformation); determination of whether insertion of the surgical object is possible based on geometric fitting of an object in accordance with compliance of adjacent tissues, which if possible, the 3D digital object is placed along with a coordinated multi-voxel tissue shift, and which if not possible, an algorithm to inform the user feedback as to why the 3D digital object will not fit along with opportunities for additional attempts for insertion of the 3D digital object or insertion of the 3D digital object with a combination of some native voxels replaced by the 3D digital object and some native voxels shifted or perform insertion of the 3D digital object with pure replacement of native voxels with voxels corresponding to the 3D digital object. Examples provided in this patent with at least some degree of deformation of native tissues include the following: insertion of a 3D digital representation of a breast implant with variable deformation of the breast; insertion of a 3D digital representation of a nasal implant with variable deformation of the nasal tissues over time; insertion of a 3D digital representation of a renal implant from a donor kidney with deformation of the adjacent adrenal gland; and, insertion of a breast mass at one time point into the same voxel space of the breast mass at a second time point with special deformation of the one of the breast masses to provide optimum comparison of how the mass changes over time. Examples provided in this patent where there is no deformation of tissues and only replacement of voxels include the following: insertion of a 3D digital object representing a radiofrequency ablation zone; insertion of a virtual coil into an aneurysm and insertion of femoral neck fixation hardware into the femur.

In accordance with an aspect a method comprises: performing filtering/segmentation, using a 3D cursor, 3D viewing via augmented reality/virtual reality headset, manipulation of voxel(s), creation of voxel(s) and elimination of voxel(s) to optimize viewing of a structure. The example provided in this patent is of a cerebral arteriovenous malformation (AVM). In this example, the feeding arteries, AVM nidus and draining veins will be labeled. Any structures that block the viewing of the AVM will be either removed or made less conspicuous. The tightly packed blood vessels will be spread apart through insertion of invisible voxels and tissue-type voxels. Through coordinated multi-voxel manipulations, voxel creation and voxel elimination, the AVM can be untangled (e.g., straightened, stretched, bent, twisted, expanded, contracted, cut, etc.) and the connections and AVM anatomy better understood. Through this virtual radiological dissection and through the insertion of dynamic voxels in the form of virtual contrast into an AVM accompanied by varying virtual occluder insertion patterns, the understanding of the complex AVM anatomy can be enhanced in a non-invasive manner.

In accordance with an aspect an apparatus comprises: an input/output (IO) device; and an image processor in communication with the IO device, the image processors comprising a program stored on computer-readable non-transitory media, the program comprising: instructions use a 3D volumetric medical imaging dataset and perform anatomic segmentation of voxels in the volumetric medical imaging dataset into distinct tissue types; assign tissue properties (mechanical properties such as elasticity, ductility, hardness or physical properties such as density or thermal conductivity) to each tissue type in the medical imaging dataset by a combination of properties acquired from the scanner and by lookup table; perform options for voxel manipulation (e.g., changing at least one voxel's size, location, orientation, shape, color/grayscale, or other voxel property); perform options for voxel creation (e.g., fixed-location voxel creation such as tissue-type or invisible-type voxel creation, dynamic voxel creation such as virtual contrast, or interactive voxel creation, such as a virtual occluder that can interact with other voxels in the 3D medical imaging); perform options for voxel elimination (e.g., eliminate and discard via volume-type elimination or surface-type elimination, cut and place voxels into a virtual specimen container bucket; perform new applications including virtual motion, deformable tissue, virtual radiological dissection, perform annotations or recording the interactive steps for replay.

In accordance with an aspect an apparatus comprises: performing of manipulation of at least one of the original voxel parameters including, but not limited to, at least one of the following: change size (e.g., increase or decrease at least one dimension of at least one voxel); change shape (e.g., change from cube shaped voxel to cylindrical shaped voxel); change in position (i.e., the center coordinate of the voxel changes in the x-direction, y-direction, and/or z-direction); change in orientation (i.e., the orientation of the voxel changes in roll, pitch and/or yaw); or change in internal parameter (e.g., texture, tissue property, etc.). Thus, at least one voxel has a final voxel parameter that differs from the original voxel parameter.

In accordance with an aspect an apparatus comprises: performing anatomic segmentation of voxels in the 3D imaging dataset, such that all voxels are assigned both a tissue type (e.g., skin, fat, bone, cerebrospinal fluid, etc.) and tissue properties (e.g., mechanical properties such as elasticity, ductility, hardness, physical properties such as density or thermal conductivity, etc.) by a combination of properties acquired from the scanner, tissue segmentation and by lookup table.

In accordance with an aspect an apparatus compromises: creation of fixed-type voxels. This implementation includes the creation of invisible-type voxels in between two closely spaced structures, such that the structures can be separated from one another. Another implementation is the creation of tissue-type voxels to stretch a structure. Another implementation is the creation of a combination of invisible-type voxels and tissue-type voxels, such that structures can be pulled apart for the purposes of untangling and better visualization of complex structures (e.g., improve visualization of a cerebral arteriovenous malformation). Other fixed-type voxels include, but are not limited to, the following: surgical-device-type voxels; fluid-type voxels (e.g., water, blood, etc.); non-fluid-type voxels (e.g., kidney tissue, etc.); or, others. This implementation includes creation of annotation-type voxels, which are attached to the structure of interest, but serve to facilitate understanding or communication of a finding. An example is annotation of voxel counting metrics, such as the markup of curvilinear distance. Note that when viewing with 3D and rotation is used, the annotations will rotate such that they are optimally viewed from each viewing perspective.

In accordance with an aspect an apparatus comprises: creation of dynamic-type voxels. This implementation includes the creation of mobile voxels, which have the capability to move through tubular shaped vascular structures from one end to another (e.g., proximal to distal) to improve visualization. The manner in which the mobile voxels move through the tubular vascular structures can be in accordance with any flow patterns, such as laminar flow or plug flow.

In accordance with an aspect an apparatus comprises: creation of interactive-type voxels. This implementation includes the creation of voxels, which have the capability to interact with any voxels or tissues within the dataset, such as placement of voxels to mimic a surgical clip and occlude the flow of virtual contrast along some portion of a tubular blood vessel. Another example is soft tissue voxels changing in relation to the placement of a virtual occluder type interactive voxels. Another example of an interactive-type voxel is the insertion of a strategic deformation voxel, which can be used to guide the deformation of soft tissue voxels when a virtual surgical object is being inserted.

In accordance with an aspect an apparatus comprises elimination of voxels in either a eliminate and discard approach (e.g., volumetric-type elimination, multi-step layer-by-layer ablative-type approach or elimination associated with the placement of a virtual object, cardinal direction-type elimination). One element to aid in the elimination of the desired voxels is through the use of strategic elimination points and strategic non-elimination points. Some implementation use a 3D cursor to eliminate voxels outside of the cursor. Some implementations use an ablative approach to take the form of elimination of the outer voxels from the whole surface, one voxel layer at a time. Other implementations with an ablative approach can take the form of elimination of the outer voxels from a portion of the whole surface, one voxel layer at a time. Other types include the elimination in accordance with placement of a virtual object.

In accordance with an aspect an apparatus comprises: performing a coordinated multi-voxel manipulation to simulate motion of anatomical structures in accordance with the intrinsic properties (e.g., hardness, elasticity, etc.) of the voxels composing the anatomic structure. Two examples were provided in this patent for illustrative purposes. The first example is virtual motion at the knee joint. The second example is the movement of a virtual catheter inside a blood vessel, with an additional viewing option to include a tunnel view (as if the viewpoint was just short of the catheter tip and viewing both the catheter tip and the branches.

In accordance with an aspect, an apparatus comprises: assignment of strategic deformation points (e.g., the user can specify which voxels are more or less deformable than predicted by the algorithm based on his/her prior knowledge to guide the coordinated multi-voxel shift to achieve the desired deformation); determination of whether insertion of the surgical object is possible based on geometric fitting of an object in accordance with compliance of adjacent tissues, which if possible, the 3D digital object is placed along with a coordinated multi-voxel tissue shift, and which if not possible, an algorithm to inform the user feedback as to why the 3D digital object will not fit along with opportunities for additional attempts for insertion of the 3D digital object or insertion of the 3D digital object with a combination of some native voxels replaced by the 3D digital object and some native voxels shifted or perform insertion of the 3D digital object with pure replacement of native voxels with voxels corresponding to the 3D digital object. Examples provided in this patent with at least some degree of deformation of native tissues include the following: insertion of a 3D digital representation of a breast implant with variable deformation of the breast; insertion of a 3D digital representation of a nasal implant with variable deformation of the nasal tissues over time; insertion of a 3D digital representation of a renal implant from a donor kidney with deformation of the adjacent adrenal gland; and, insertion of a breast mass at one time point into the same voxel space of the breast mass at a second time point with special deformation of the one of the breast masses to provide optimum comparison of how the mass changes over time. Examples provided in this patent where there is no deformation of tissues and only replacement of voxels include the following: insertion of a 3D digital object representing a radiofrequency ablation zone; insertion of a virtual coil into an aneurysm and insertion of femoral neck fixation hardware into the femur.

In accordance with an aspect an apparatus comprises: performing filtering/segmentation, 3D cursor, 3D viewing via augmented reality/virtual reality headset, manipulation of voxel(s), creation of voxel(s) and elimination of voxel(s) to optimize viewing of a structure. The example provided in this patent is of a cerebral arteriovenous malformation (AVM). In this example, the feeding arteries, AVM nidus and draining veins will be labeled. Any structures that block the viewing of the AVM will be either removed or made less conspicuous. The tightly packed blood vessels will be spread apart through insertion of invisible voxels and tissue-type voxels. Through coordinated multi-voxel manipulations, voxel creation and voxel elimination, the AVM can be untangled (e.g., straightened, stretched, bent, twisted, expanded, contracted, cut, etc.) and the connections and AVM anatomy better understood. Through this virtual radiological dissection and through the insertion of dynamic voxels in the form of virtual contrast into an AVM accompanied by varying virtual occluder insertion patterns, the understanding of the complex AVM anatomy can be enhanced in a non-invasive manner.

In accordance with an aspect a computer-readable medium comprises: instructions which, when executed by a computer, cause the computer to carry out the steps of: assigning tissue type properties to voxels of a medical image; and performing a three-dimensional simulation by manipulating the voxels based on the assigned tissue type properties and an input that prompts voxel manipulation. In some implementations the step of assigning tissue type properties to the voxels of the medical image comprises assigning a value for at least one of: elasticity, ductility, hardness, density, and thermal conductivity. In some implementations the step of manipulating the voxels comprises changing at least one of voxel size, voxel location, voxel orientation, voxel shape, voxel color, voxel grayscale, and voxel tissue type property value. In some implementations the input comprises inserting a virtual volume-subtending surgical object. In some implementations the input comprises inserting a virtual volume-subtending anatomic object. In some implementations the step of performing the simulation comprises representing virtual motion. In some implementations the step of performing the simulation comprises representing deformation of tissue. In some implementations the step of performing the simulation comprises representing a radiological dissection. In some implementations the step of performing the simulation comprises creating new voxels in response to the input. In some implementations the step of creating new voxels comprises creating new fixed-type voxels that do not change unless acted upon by a user through an interface. In some implementations the step of creating new voxels comprises creating new invisible-type voxels. In some implementations the step of creating new voxels comprises creating new tissue-type voxels. In some implementations the step of creating new voxels comprises creating new dynamic-type voxels having at least one tissue type property that changes over time. In some implementations the step of creating new voxels comprises creating new mobile voxels that travel through a virtual vascular structure. In some implementations the step of performing the simulation comprises eliminating selected voxels in response to the input. In some implementations the instructions comprise eliminating tissue type voxels to simulate ablation. In some implementations the instructions comprise inserting strategic elimination points that designate a direction in which voxels are eliminated in discrete steps. In some implementations the instructions comprise inserting strategic non-elimination points that designate voxels that are preserved from elimination. In some implementations the instructions comprise assignment of a strategic deformation feature that designates a maximum shift for at least one voxel.

In some implementations, a method comprises: generating a 3D volumetric dataset through an artificial intelligence process; assigning at least one mechanical type property to the 3D volumetric dataset; performing rendering of the 3D volumetric wherein the 3D volumetric dataset has a first configuration; receiving an input to cause the 3D volumetric dataset to change from a to a subsequent configuration wherein the change to a subsequent configuration is in accordance with the nature of the input and the mechanical type properties of the 3D volumetric dataset; changing the 3D volumetric dataset from a first configuration to the subsequent configuration; and performing rendering of the 3D volumetric dataset in the subsequent configuration.

The preferred method of generating a 3D volumetric dataset through an artificial intelligence process is through a generative adversarial network. A generative adversarial network can generate and discriminate real vs. fake data. Please see U.S. patent application Ser. No. 16/703,629 titled Radiologist-assisted machine learning with interactive, volume-subtending 3D cursor filed on 4 Dec. 2019 for additional details on generating of a 3D volumetric dataset. The preferred embodiment is to generate the full set of data including every internal anatomic feature to the best possible detail (i.e., equal to that of an actual scan), which will allow using this data for purposes such as building training datasets for machine learning purposes in diagnostic radiology. An alternative embodiment, is to build only selected portions of the internal volumes using artificial intelligence process. For example, if the rendering (see below) was only going to be done of the skin surface, building the intricate internal volumes inside the bone for example would not contribute to the actual rendering. However, building the fat, muscle, tendons, ligaments and outer surfaces of the bone would be useful for rendering purposes as realistic shapes could be formed. This embodiment reduces demand on CPUs and GPUs.

The preferred embodiment of assigning at least one mechanical type property to the 3D volumetric dataset includes a voxel based assignment. Specifically, each voxel would be assigned a tissue type and each tissue type would have a specific set of mechanical properties. This is useful because voxels could be manipulated, as discussed above, and simulations could be performed. For example, consider assigning a rigid property to the mandible and a flexible property to the cheeks and lips. During a wide opening of the mouth, the muscles contract, the rigid mandible moves downward and the cheeks and lips stretch to the new configuration. Thus, by assigning mechanical type properties to each voxel, simulations can be performed.

The preferred embodiment of performing rendering is through the D3D process, as first described in U.S. Pat. No. 8,384,771 Method and apparatus for three-dimensional viewing of images. In this disclosure, a head display unit performs stereoscopic rendering and voxel filtering. This allows a user to see exactly the tissues of interest and eliminate the tissues of non-interest. Note that this initial performing rendering of the 3D volumetric is wherein the 3D volumetric dataset has a first configuration.

Next, the preferred embodiment of receiving an input to cause the 3D volumetric dataset to change from a to a subsequent configuration wherein the change to a subsequent configuration is in accordance with the nature of the input and the mechanical type properties of the 3D volumetric dataset is discussed. The preferred embodiments include intrinsic alterations (e.g., via muscular contraction, flow down pressure gradients, etc.). A first source of inputs of movement will be via muscular contractions is discussed. Thus, each muscle will be modeled with its origin at a first set of (x, y, z) coordinates, which connects to bone and its insertion at a second set of (x, y, z) coordinates which connects to a similar spot on a different portion of bone or a different bone altogether. During a muscular contraction, the muscle fibers thicken and shorten. A single coordinate system could be performed. For example, bone has its center coordinate with roll, pitch and yaw. Unless fractured, drilled or the like, bones would always maintain the same configuration. For example, muscles would have a origin and insertion on the bones, but their configuration would change in relation to contractions. In addition, during muscular contractions, the position and orientation of the bones would also change. In some embodiments, a series of coordinate systems can be implemented to achieve and model complex movements. In contrast to a single master coordinate system (e.g., all voxels in the entire human body are plotted onto a single coordinate system), another embodiment is for one coordinate system could be established for each bone since bones are rigid structures. For example, the scapula would have a first coordinate system. The humerus would have a second coordinate system. The radius would have a third coordinate system. And so on. For example, see 62/939,685, Method and apparatus for development of an organ-specific coordinate system for additional details. Other methods can be used for fluids (e.g., blood flow), which occurs down pressure gradients. The alternative embodiment is to have inputs be from external sources. Some implementation comprise wherein a force from a first 3D object causes a second 3D object to deform. For example, a hard object can push on a deformable object, such that the hard object does not deform and the deformable object does deform. For example, a virtual surgical device could be pressed against a soft tissue structure, which causes it to deform.

The preferred embodiment for changing the 3D volumetric dataset from a first configuration to the subsequent configuration is to generate a new voxelated dataset with a specific time step. For example, 60 datasets could be generated per second (60 Hz) over a muscular contraction. The preferred embodiment is for a large number of datasets to be generated. Alternative embodiments would be to have a beginning pre-contraction image, a mid-contraction image and a post-contraction image.

The preferred embodiment of performing rendering is through the D3D process, as first described in U.S. Pat. No. 8,384,771 Method and apparatus for three-dimensional viewing of images. Note that rendering of fluids can also be performed as described in U.S. provisional patent No. 62/906,125, A method and apparatus for stereoscopic rendering of mobile fluids. Some implementation comprise generating virtual contrast.

Some implementation comprise performing voxel manipulation to achieve the subsequent configuration by changing at least one of voxel size, voxel location, voxel orientation, voxel shape, voxel color, voxel grayscale, and voxel tissue type property value.

Some implementation comprise generating a 3D volumetric dataset comprised of voxels with at least two different tissue type properties. Some embodiments comprise generating a 3D volumetric dataset comprised of voxels with at least two different tissue type properties. For example, a simple model would be rigid bone structures and flexible soft tissues. For example, these two types of structures together could build a simulated face. However, additional tissue type properties would be needed for best modeling, to include muscles, fat, cartilage, etc. Other examples include bending of a knee, opening of a hand, and movements of a face.

Some implementation comprise an artificial intelligence process that uses a generative adversarial network. See U.S. patent application Ser. No. 16/703,629 for additional details.

Some implementation comprise performing advanced visualization techniques comprising at least one of rotation, zoom, filtering, segmentation, false color, prioritized volume rendering, and texture. Some embodiments comprise performing additional techniques, such as advanced visualization, as described in: Some of the techniques in this patent are performed by utilizing techniques described in: U.S. patent application Ser. No. 15/878,463, Interactive 3D cursor for use in medical imaging; U.S. patent application Ser. No. 16/010,925, Interactive placement of a 3D digital representation of a surgical device or anatomic feature into a 3D radiologic image for pre-operative planning; U.S. patent application Ser. No. 15/904,092, Processing 3D medical images to enhance visualization; U.S. patent application Ser. No. 15/949,202, Smart operating room equipped with smart surgical devices; U.S. Pat. No. 9,473,766, Method and apparatus for three dimensional viewing of images; U.S. Pat. No. 9,615,806, Method and apparatus for creation and display of artifact corrected three dimensional (3D) volumetric data from biplane fluoroscopic image acquisition; U.S. patent Ser. No. 14/644,489, Method and apparatus for creation and display of artifact corrected three dimensional (3D) volumetric data from biplane fluoroscopic image acquisition; U.S. Pat. No. 9,980,691, Method and apparatus for three dimensional viewing of images; U.S. Pat. No. 9,349,183, Method and apparatus for three dimensional viewing of images; U.S. patent application Ser. No. 16/509,592, Implantable markers to aid surgical operations; U.S. patent application Ser. No. 16/524,275, Using geo-registered tools to manipulate three-dimensional medical images; PCT/US19/478, A virtual tool kit for radiologists; U.S. patent application Ser. No. 16/594,139, Method and apparatus for performing 3D imaging examinations of a structure under different configurations and analyzing morphologic changes; U.S. patent application Ser. No. 16/683,256, Method and apparatus for performing 3D imaging examinations of a structure under different configurations and analyzing morphologic changes; U.S. provisional application No. 62/843,612, A method of creating a computer-generated patient specific image; U.S. provisional application No. 62/846,770, A method of prioritized volume rendering to improve visualization of prioritized items within a 3D volume; U.S. provisional application No. 62/850,002, A method of creating an artificial intelligence generated differential diagnosis and management recommendation tool boxes during medical personnel analysis and reporting; U.S. patent application Ser. No. 16/654,047, A method to modify imaging protocols in real time through implementation of artificial intelligence; U.S. provisional application No. 62/856,185, A method of image manipulation based on eye tracking; U.S. patent application Ser. No. 16/506,073, A method for illustrating direction of blood flow via pointers; U.S. patent application No. 62/906,125, A method and apparatus for stereoscopic rendering of mobile fluids; and, U.S. patent application No. 62/939,685, Method and apparatus for development of an organ-specific coordinate system.

Some implementation comprise wherein the 3D dataset is a 3D object. Examples include any tangible object, such as bone, muscle, surgical instrument, tumor, or other non-medical related tangible objects.

Some implementation comprise creating at least two different 3D objects. Such objects can be a wide range of anatomic, surgical or other tangible devices. Some implementation comprise wherein the at least two different 3D objects are moved from a first position when the at least two different 3D objects are separate to a second position wherein the at least two different 3D objects are touching.

Some implementation comprise a time stepped interactive feature, as is described in greater detail in U.S. patent application Ser. No. 16/563,985, A method and apparatus for the interaction of virtual tools and geo-registered tools. Some implementation comprise an educational simulation for surgical steps. Some implementation comprise interaction with sound and tactile feedback.

Some implementation comprise wherein the 3D dataset has tissue type properties to mimic at least one pathology. For example, some cancers, such as breast cancers are hard. Lipomas are soft. DVTs are hard. Infections cause induration. Abscesses are fluctuant.

Some embodiments comprises an artificial intelligence process that use a generative adversarial network. For example, techniques can be used, such as is described in U.S. patent application Ser. No. 16/703,629, Radiologist-assisted machine learning with volume-subtending 3D cursor.

Some embodiments comprise performing inputs to mimic muscular contractions, including at least one of the group comprising: bending of a knee; opening of a hand; and, movements of a face. For example, complex movements could achieve lifelike appearances moving in 4D, such as a person talking or a person walking.

DETAILED DESCRIPTION

Figure 1:
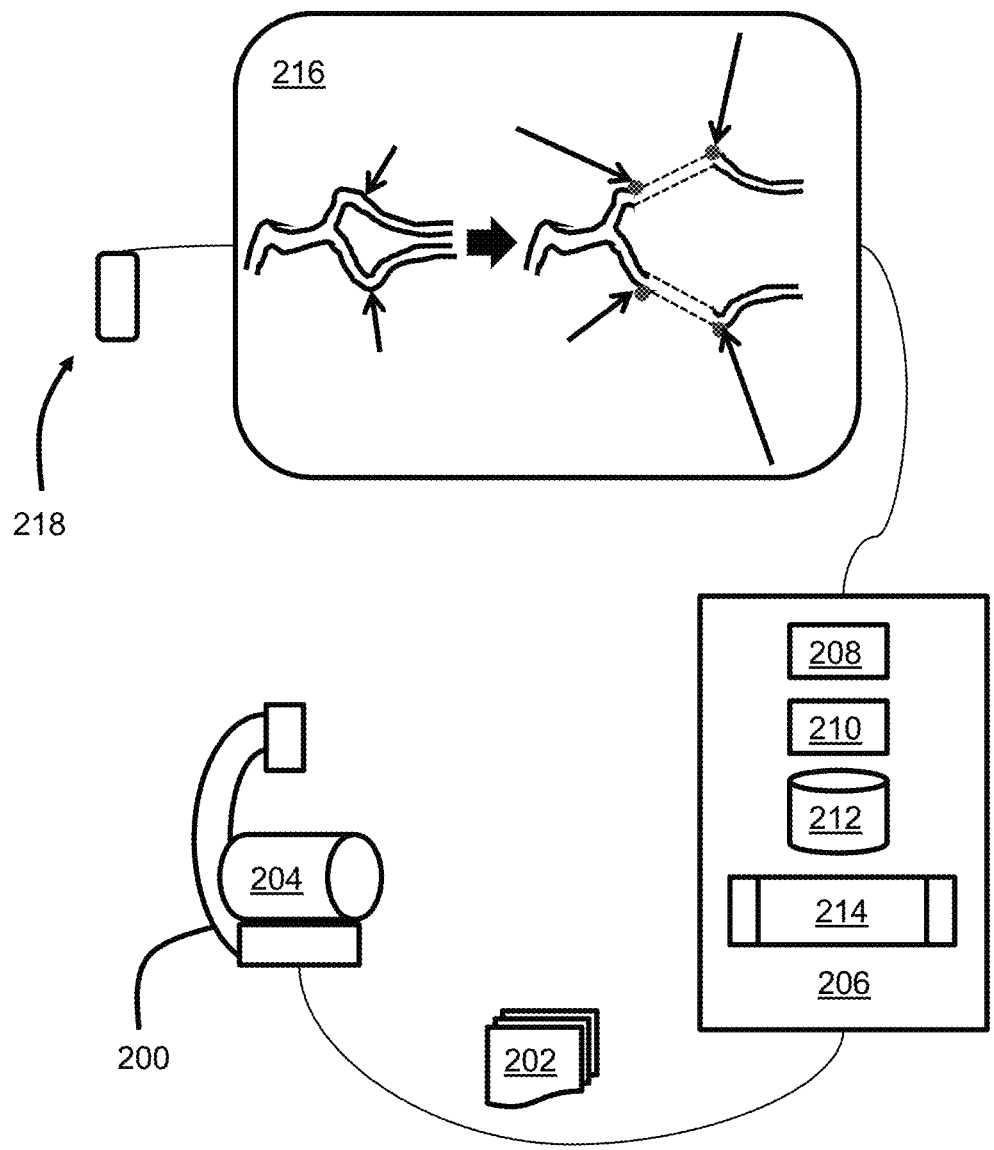
FIG. 1 illustrates an apparatus for surgical planning.

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

The terminology used in this disclosure is intended to be interpreted broadly within the limits of subject matter eligibility. The terms "logical" and "virtual" are used to refer to features that are abstractions of other features, e.g. and without limitation abstractions of tangible features. The term "physical" is used to refer to tangible features. For example, multiple virtual computing devices could operate simultaneously on one physical computing device. The term "logic" is used to refer to special purpose physical circuit elements and software instructions that are stored on a non-transitory computer-readable medium and implemented by multi-purpose tangible processors.

The following are incorporated by reference:
U.S. Provisional Patent Application 62/628,527 titled A METHOD AND APPARATUS FOR INTERACTIVE PLACEMENT OF A DIGITAL REPRESENTATION OF A SURGICAL DEVICE INTO RADIOLOGIC IMAGES, filed Feb. 9, 2018;
U.S. Provisional Patent Application 62/695,868 titled INTERACTIVE VOXEL MANIPULATION STRATEGIES IN VOLUMETRIC MEDICAL IMAGING ENABLES VIRTUAL MOTION, DEFORMABLE TISSUE, AND VIRTUAL RADIOLOGICAL DISSECTION, filed Jul. 10, 2018;
U.S. patent application Ser. No. 15/904,092 titled PROCESSING 3D MEDICAL IMAGES TO ENHANCE VISUALIZATION, filed Feb. 23, 2018;
U.S. patent application Ser. No. 16/010,925 titled INTERACTIVE PLACEMENT OF A 3D DIGITAL REPRESENTATION OF A SURGICAL DEVICE OR ANATOMIC FEATURE INTO A 3D RADIOLOGIC IMAGE FOR PRE-OPERATIVE PLANNING, filed Jun. 18, 2018, which is a non-provisional of U.S. 62/628,527;
U.S. Pat. No. 8,384,771 titled METHOD AND APPARATUS FOR THREE DIMENSIONAL VIEWING OF IMAGES; and
U.S. Pat. No. 9,980,691 titled METHOD AND APPARATUS FOR THREE DIMENSIONAL VIEWING OF IMAGES.

U.S. 62/628,527 describes insertions of 3D digital objects into volumetric medical images to improve pre-operative planning. The 3D digital objects are superimposed on the volumetric medical images, such as where both an object and a portion of anatomy share the same image coordinates. Adjusting the transparencies of the object and anatomy enables both the anatomy and the inserted object to be contemporaneously visualized. However, distortion of anatomic tissues resulting from insertion of a volume-subtending digital surgical or anatomic object is not represented by superimposition. It would therefore be useful to have a process to determine how to displace native voxels corresponding to displacement of native tissues, including how those native voxels are distorted when a new digital surgical or anatomic object is inserted.

Radiological imaging modalities including computed tomography (CT), magnetic resonance imaging (MRI), single photon emission computed tomography (SPECT), and positron emission tomography (PET) all acquire volumetric medical imaging datasets and traditionally present these datasets in a slice-by-slice manner. Techniques from U.S. Pat. Nos. 8,384,771, 9,980,691, U.S. patent application Ser. No. 15/904,092, and U.S. patent application Ser. No. 16/010,925, each of which is incorporated by reference, describe processes for building a volumetric 3D dataset and enhanced viewing methods including a head display unit (HDU) such as an augmented reality (AR) or virtual reality (VR) headset, 3D cursor, and other enhanced viewing methods. Aspects of these processes may be combined, augmented, and improved upon to enable virtual motion, deformable tissues, and virtual radiological dissection through manipulation of voxels.

In some implementations virtual motion is achieved by assigning material-like properties in the voxel manipulation process. Tissue properties possibly including, but not limited to, mechanical properties such as elasticity, ductility, hardness, and physical properties such as density and thermal conductivity, may be used to calculate displacement of native voxels corresponding to tissue distortion. Soft tissues can be assigned a deformable tissue property and bones can be assigned a rigid-type tissue property, to match what naturally occurs. An application of the process is representing tissue deformation during placement of a 3D virtual object into a 3D medical imaging dataset. To guide the deformation process, strategic deformation points (or voxels) can be assigned.

Another limitation that exists in 3D medical imaging is the lack of ability to represent complex 3D anatomy due to proximity between multiple branches of an anatomical feature. An example clinical scenario is a cerebral arteriovenous malformation where this limitation of complex 3D anatomy and multiple vessels in close proximity may significantly impact patient care by hindering neurosurgical and neuro-interventional radiology's decision making. If the precise anatomy could be better understood, then decision-making and treatment planning could be improved, possibly along with improved outcomes. Voxel manipulation, creation, and elimination can be utilized together to perform a virtual radiological dissection, for which the example discussed in detail herein is the untangling of a complex cerebrovascular arteriovenous malformation. A single voxel or group of voxels can be annotated to improve the radiological dissection process. Furth, the interactive voxel manipulation steps can be recorded and re-played from any angle to improve representation and understanding of complex anatomy.

FIG. 1 illustrates an apparatus for implementing virtual motion, deformable tissues, and virtual radiological dissection through manipulation of voxels. A radiologic imaging system 200 (e.g., X-ray, ultrasound, CT (computed Tomography), PET (Positron Emission Tomography), or MRI (Magnetic Resonance Imaging)) is used to generate 2D medical images 202 of an anatomic structure 204 of interest. The 2D medical images 202 are provided to an image processor 206, that includes processors 208 (e.g., CPUs and GPUs), volatile memory 210 (e.g., RAM), and non-volatile storage 212 (e.g. HDDs and SSDs). A program 214 running on the image processor implements one or more steps as described below, e.g. and without limitation to generate simulations. 3D medical images are generated from the 2D medical images and displayed on an IO device 216. The IO device may include a virtual or augmented reality headset, monitor, tablet computer, PDA (personal digital assistant), mobile phone, or any of a wide variety of devices, either alone or in combination. The IO device may include a touchscreen and may accept input from external devices (represented by 218) such as a keyboard, mouse, and any of a wide variety of equipment for receiving various inputs. However, some or all the inputs could be automated, e.g. by the program 214.

Figure 2:
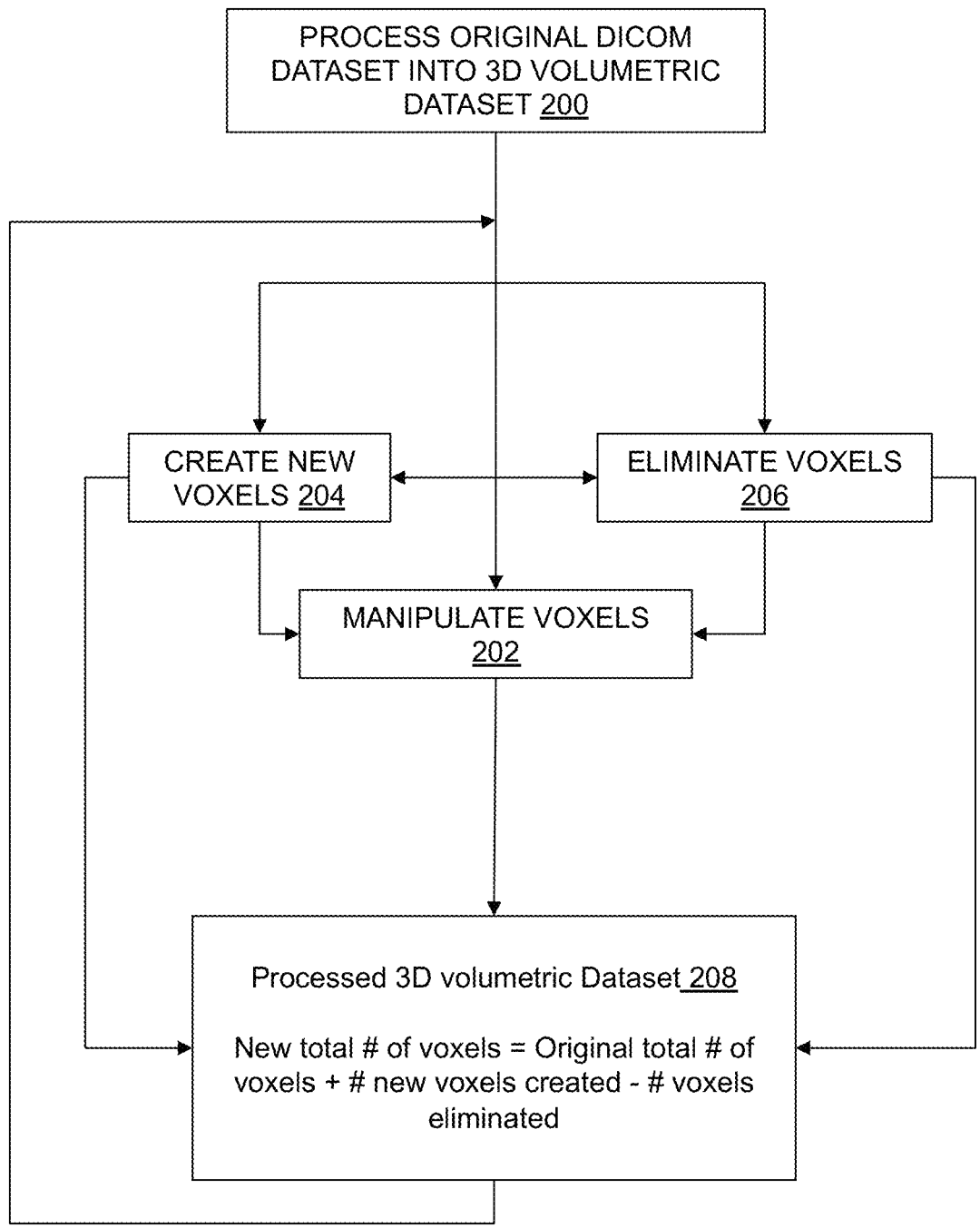
FIG. 2 illustrates voxel manipulation, creation, and elimination processes that improve visualization of an anatomic structure.

FIG. 2 illustrates aspects of voxel processing by program 214 (FIG. 1). Input voxels of DICOM (Digital Imaging and Communications in Medicine) images are used to generate a 3D volumetric dataset as indicated in block 200. The 3D volumetric dataset is characterized by an initial total voxel number and initial voxel properties, which may be assigned. The 3D volumetric dataset undergoes one or more of voxel manipulation 202, voxel creation 204, and voxel elimination 206, in any combination, any order, and any number of iterations. The result of the processing is a processed 3D volumetric dataset 208, for which total voxel number and voxel properties are altered relative to the input 3D volumetric dataset. Single voxel-manipulation and coordinated multi-voxel manipulation in step 202 may include: alteration of voxel size; alteration of voxel location; alteration of voxel orientation; alteration of voxel shape; alteration of voxel internal parameters (e.g., gray-scale, color, tissue properties, mechanical properties, physical properties, etc.). Voxel creation in step 204 may include, but is not limited to, fixed-voxel creation (e.g., surgical-device-type voxels, tissue-type voxels, invisible-type voxels, etc.), dynamic voxels (e.g., mobile voxels such as virtual contrast), and interactive voxels (e.g., strategic deformation points, strategic elimination points, virtual occluder, etc.). Voxel elimination in step 206 may include, but is not limited to, the following: an eliminate and discard-type approach (e.g., volume-type elimination, surface-type elimination), and elimination with placement of eliminated voxels into the virtual specimen container bucket.

Figure 3:
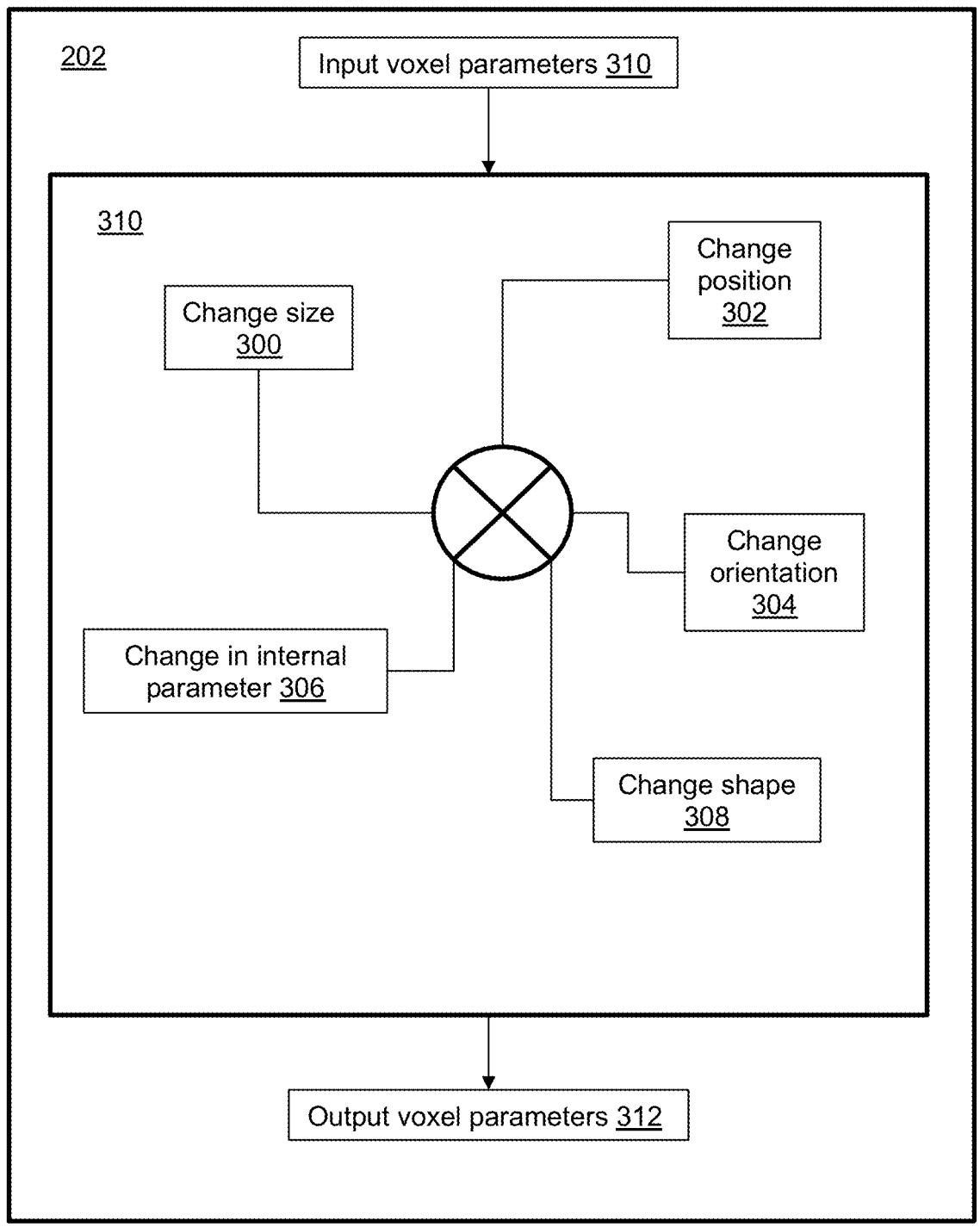
FIG. 3 illustrates aspects of voxel manipulation in greater detail, including change in voxel size, shape, position, orientation, or internal parameter.

FIG. 3 illustrates aspects of the voxel manipulation process 202 in greater detail. Aspects include one or more of size changes 300, position changes 302, orientation changes 304, internal parameter changes 306, and shape changes 308, in any combination 310. Changing voxel size 300 includes increasing or decreasing the notional volume of a selected voxel. Changing voxel position 302 includes reconfiguring the location of the selected voxel, e.g. by changing the X, Y, Z coordinates corresponding to a center point of the voxel. Changing voxel orientation 304 includes altering one or more of the roll, pitch, and yaw of the selected voxel relative to a point of reference. Changing internal parameters 306 includes adjusting assigned values related to visualization, e.g., color, gray-scale, texture, etc., values related to physical properties, and values related to mechanical properties. Changing shape 308 includes altering the geometric shape of the selected voxel, e.g., cylinder, cone, sphere, cuboid, etc. The combination of changes converts the input set of voxel parameters 310 into an output set of voxel parameters 312.

Figure 4:
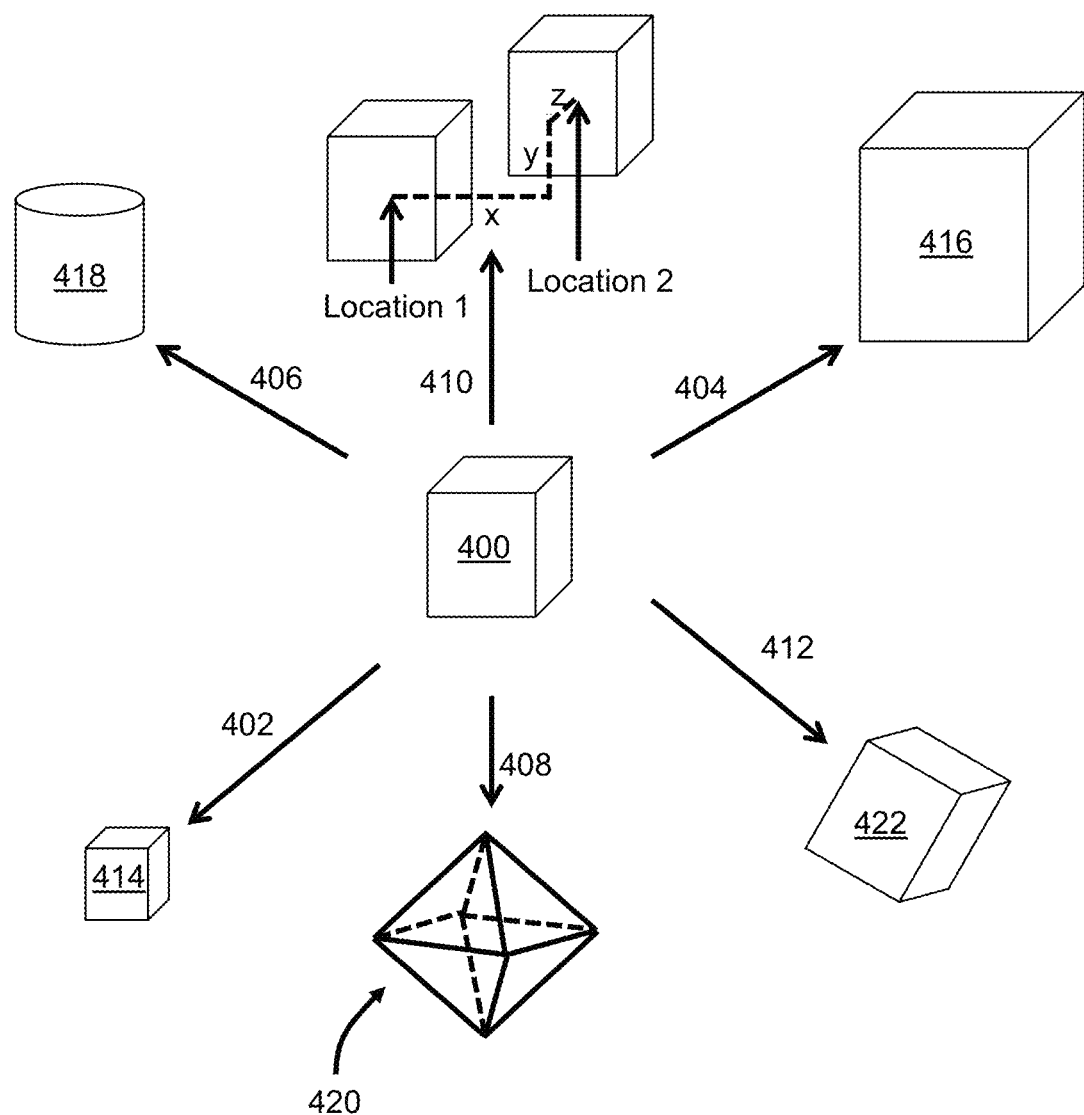
FIG. 4 illustrates examples of a single voxel manipulation with change in voxel size, shape, position, orientation, or internal parameter.

FIG. 4 illustrates aspects of manipulation of a single voxel in greater detail. Voxel manipulation is illustrated with respect to an input voxel 400 having a cuboid shape. A manipulation 402 that decreases the size (volume) of the input voxel ratiometrically decreases the lengths of edges of the voxel such that the shape of a resulting voxel 414 is scaled-down. A manipulation 404 that increases the size of the input voxel ratiometrically increases the lengths of edges of the voxel 400 such that the shape of the resulting voxel 416 is scaled-up. A manipulation 406 that alters the shape of the voxel 400 into a cylinder results in a cylindrical voxel 418 characterized by the same volume, location, and orientation as the input voxel. A manipulation 408 that alters the shape of the voxel into an octahedron results in a voxel 420 characterized by the same volume, location, and orientation as the input voxel. A manipulation 410 of the center point of the voxel results in movement from location 1 to location 2 within the 3D medical image. A manipulation 412 of the orientation of the input voxel alters orientation while retaining shape, size and center point location, resulting in voxel 422. As already mentioned, the changes may be implemented in combination, e.g. in series. Because the spatial resolution of many examinations (e.g., CT or MRI) is 1 mm or smaller, small structures can have a poor aesthetic appearance. Take for example, a 3 mm blood vessel making a 180 degree turn over 1 cm. A voxel transformation from cube-shape to cylindrical-shaped voxels would constitute an improvement of visualization. It is anticipated that performing voxel transformations to improve visualization will directly improve diagnosis and patient care.

In the context of a 3D image, manipulation of a single voxel may prompt manipulation of adjacent voxels (unless there is empty space adjacent to the changed voxel). For example, changes to one or more of size, shape, orientation, and location of the center point of the voxel may affect adjacent voxels. The way the adjacent voxels are affected is determined at least in part by the internal parameters of the adjacent voxels. FIGS. 5A, 5B, 5C, and 5D illustrate examples of coordinated multi-voxel manipulation, including twisting, bending, straightening, and shrinking.

Figure 5A:
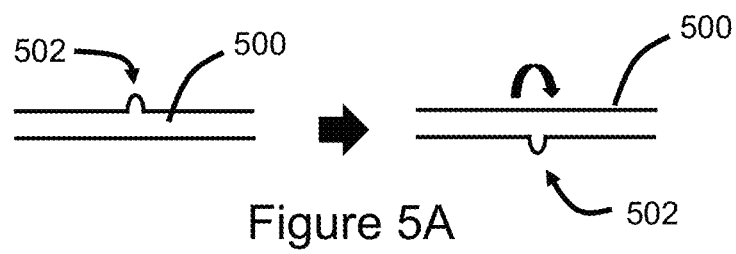
FIGS. 5A, 5B, 5C, and 5D illustrate examples of coordinated multi-voxel manipulation, including twisting, bending, straightening, and shrinking.

Referring to FIG. 5A, virtual object twisting based on multi-voxel manipulation can be used to improve visualization. For example, the user may prompt twisting of a structure about its axis, such as performing roll, pitch, and yaw manipulations, or any combination thereof, or in combination with other voxel manipulations, voxel insertions, or voxel removals. In the illustrated example a blood vessel 500 with a small aneurysm 502 is rotated. As a result, the aneurism is relocated from top to bottom in the image. Assigned intrinsic tissue properties will determine the maximum amount of twist. During the twisting process, the coordinates of the whole twisted vessel undergo a transformation in accordance with the amount of twist. Additional twisting algorithms may include, but are not limited to, the following: center of the vessel twists a greater rotation than the off-center portions of the vessel; and, free ends (e.g., cut ends) of the vessel twists a greater rotation than other portions of the vessels. In conjunction with other voxel manipulations and insertions described herein, a virtual twisting procedure may prove beneficial in improving understanding of a complex cerebral AVM (arteriovenous malformation).

Figure 5B:
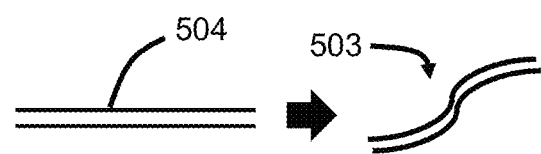

FIG. 5B illustrates use of multi-voxel location and orientation manipulation to improve visualization. In the illustrated example voxel manipulation is used to generate a bend 503 in a straight blood vessel 504. The bend is generated without stretching the feature being manipulated unless limited stretching is indicated by internal properties. This may be useful for untangling features in a complex image.

Figure 5C:

FIG. 5C illustrates another use of location and orientation manipulation to improve visualization. In the illustrated example voxel manipulation is used to straighten a non-linear section of a blood vessel 506, resulting in linear section 507. The change may be implemented without stretching the feature being manipulated unless limited stretching is indicated by internal properties. This may be useful for untangling features in a complex image.

Figure 5D:
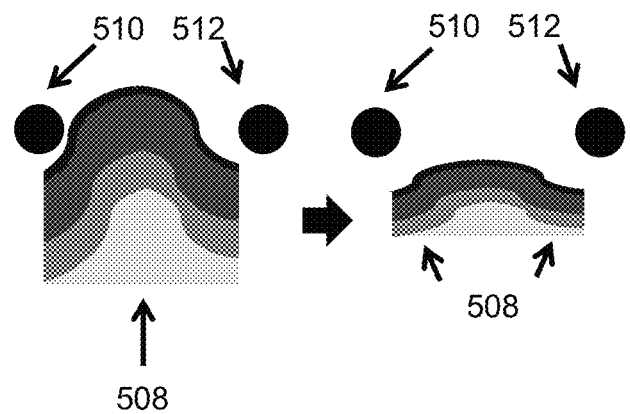

FIG. 5D illustrates use of deformation and shrinking manipulations to improve visualization of features of interest. In the illustrated example, a gyrus 508 of the brain is obscuring visualization of blood vessels 510, 512. The user can, via the IO device, shrink or deform the gyrus 508 such that the viewing of the blood vessels 510, 512 is optimized. The voxels of the gyrus are manipulated by shrinking of voxel size and changing voxel location. The illustrated example depicts the gyrus on end, disposed between the two blood vessels. The whole gyrus (i.e. all layers) is shrunk such that the blood vessels can be better visualized depending on the viewing perspective. More particularly, the cluster of voxels associated with the gyrus is deformed by changes in size, shape, and orientation of gyrus voxels to account for the downward deformation, as are adjacent clusters of voxels. It should be noted that although the shape, orientation, location, and size of the voxels may be changed, voxels have not been subtracted. It will therefore be understood that deformation is not the same as subtraction. The result of the illustrated tissue deformation is that the two parallel vessels are in line of sight from one another, without the gyrus being disposed therebetween. A wide variety of voxel deformation manipulations are possible including, but not limited to, the following: shrinking or expanding a cluster of voxels based on their location; shrinking or expanding a cluster of voxels based on by tissue type; and, altering the location of a portion of voxels, such as would be done if a rigid object was pushing onto the gyrus of the brain. The ability to deform a structure helps to overcome an appreciable set of limitations in medical imaging, which includes in the illustrated example the current limitation of one tissue type obscuring another.

To represent deformation of tissues, each tissue type in the body is assigned a tissue property of rigidness. Bone, for example, is highly rigid, whereas brain tissue is moderately rigid, and unclotted blood is fluid with no internal rigidity. In some implementations, highly rigid structures cannot be deformed, but may be altered via drilling methods. Structures of medium rigidity containing voxels within layers of the tissue could be deformed such that during the deformation the overall integrity between the tissue layers remains unaltered, but the relative size or number of voxels can be decreased in one area but increased in another area. As an example, in gross anatomy it is possible to push with the finger downward to deform the shape of the gyrus of brain such that it takes on a more flattened appearance but preserves the tissue layers. Some implementations simulate such deformation.

Figure 6:
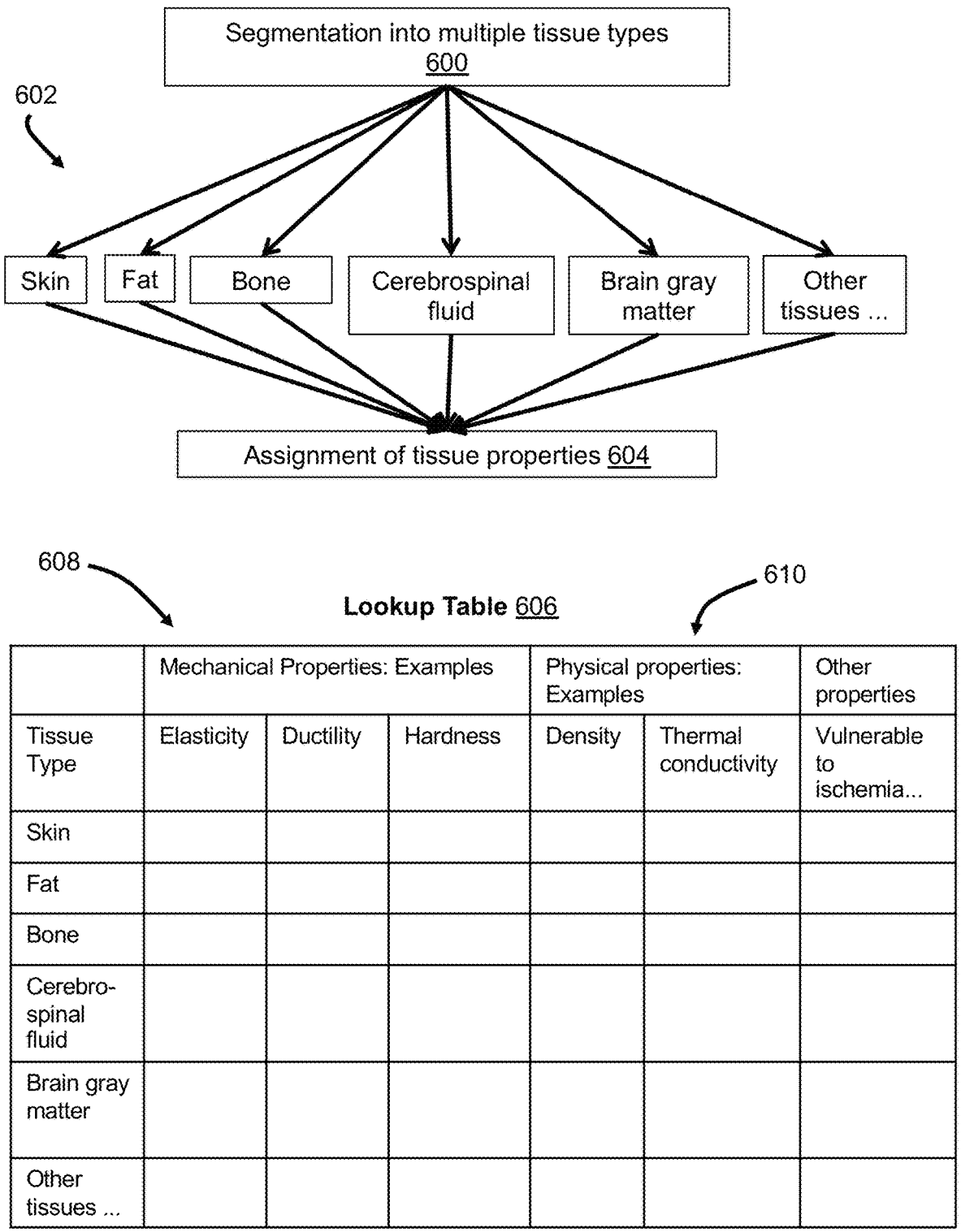
FIG. 6 is a flow diagram that illustrates segmentation of voxels into tissue types along with a look-up table of voxel parameters for specific tissue types.

FIG. 6 illustrates a process for assignment of voxel internal properties. An image or portion thereof (e.g. volume of interest) is segmented into tissue types as indicated in step 600. In the illustrated example the tissue types 602 are skin, fat, bone, cerebrospinal fluid, brain gray matter, and other tissues. Values associated with different types of properties are then assigned to the voxels of each tissue type as indicated in step 604. The values may be recorded in, and retrieved from, a look-up table 606. The illustrated look-up table includes values for mechanical properties 608 and physical properties 610. The mechanical properties include elasticity, ductility, and hardness. The physical properties include density and thermal conductivity. Other properties, e.g. chemical properties, may also be included. The parameter values are used to calculate voxel manipulations associated with tissue deformation, and thereby determine whether the represented tissues will deform in a realistic manner. As an example, skin should be assigned some intrinsic elasticity whereas bone should be assigned a rigid-type property rather than an elastic-type property. As another example, cortical bone should be assigned a high level of hardness and cartilage should be assigned a lower level of hardness.

Figure 7:
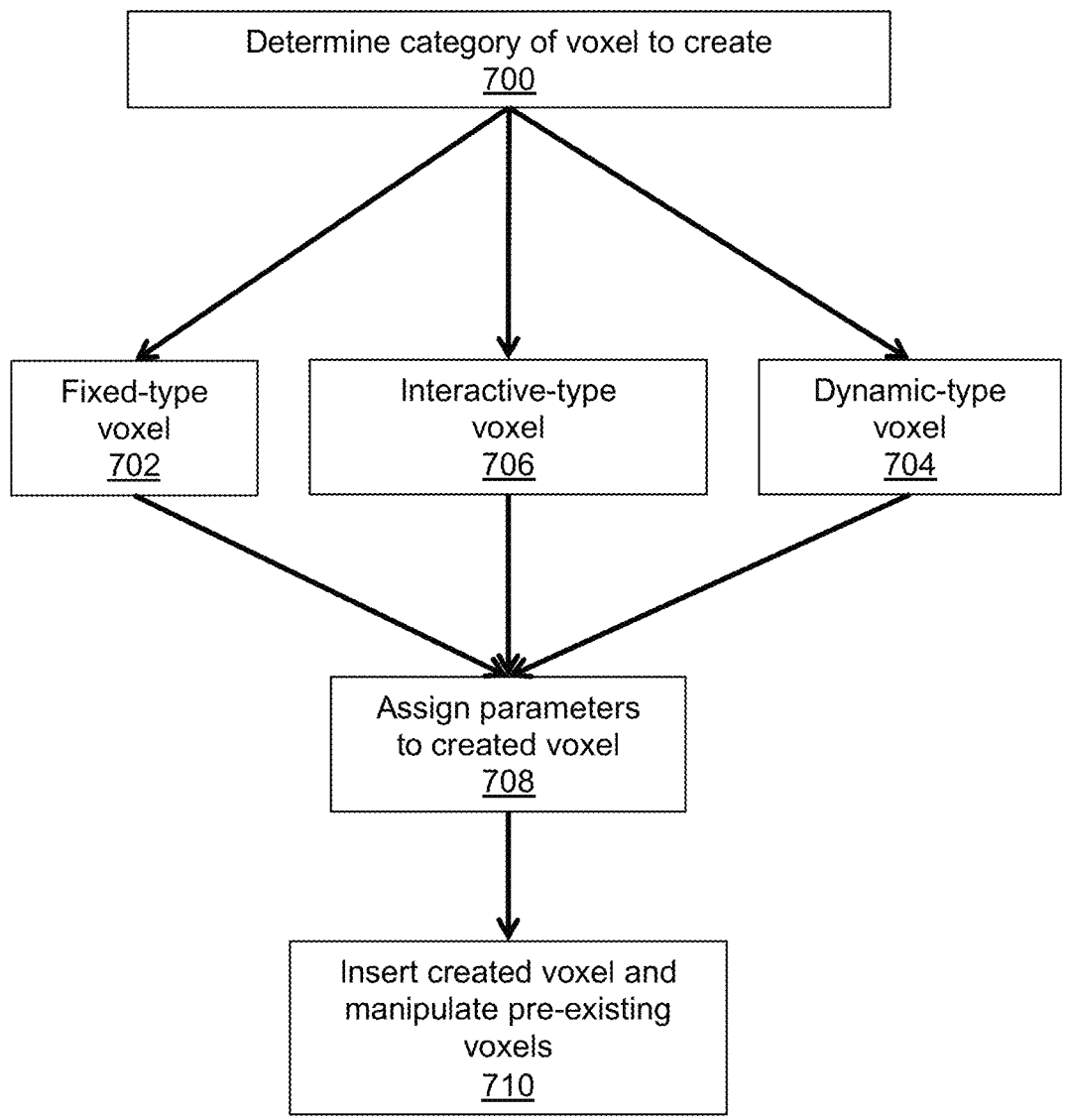
FIG. 7 is a flow diagram that illustrates new voxel creation in greater detail, including fixed-type voxels, dynamic-type voxels and interactive-type voxels.

FIG. 7 illustrates aspects of the voxel creation process. The first step 700 is to determine which category of voxel to create. The categories of voxels include fixed-type voxels 702, dynamic-type voxels 704, and interactive-type voxels 706. Fixed-type voxels do not change unless acted upon by the user through the IO device. Fixed-type voxels may be present in the original DICOM data and may be created. Examples of fixed-type voxels include, but are not limited to, the following: surgical-device-type voxels; tissue-type voxels; invisible-type voxels; common material-type voxels (e.g., water, air, etc.); and, many others. Dynamic-type voxels have at least one parameter that changes over time in a prescribed manner unless acted upon by the user. Dynamic-type voxels do not exist in the original DICOM data but can be created by the user. Examples of dynamic-type voxels include, but are not limited to, the following: virtual contrast where the position of the voxels changes over time to simulate blood flow; and, mobile objects, such as a 3D digital representation of a heart valve, which would open and close in accordance with the heart beats. Interactive-type voxels can change fixed-type voxels and dynamic-type voxels in at least one way. Interactive-type voxels do not exist in the original DICOM data but can be created. Examples of interactive-type voxels include, but are not limited to, the following: virtual occluder which stops the movement of virtual contrast within a blood vessel; strategic deformation points which helps guide the process of voxel manipulation (e.g., local tissue distortion when inserting a 3D digital object); strategic elimination points which helps to guide the elimination of voxels of non-interest; or others. After determining the category of voxel to create, corresponding parameters (e.g., size, shape, position, orientation, internal parameter, etc.) are assigned to the voxel as indicated in step 708. The created voxels are then inserted into the medical imaging data set as indicated at step 710. The insertion step includes manipulation of pre-existing voxels (i.e., those in place prior to the insertion).

Figure 8A:
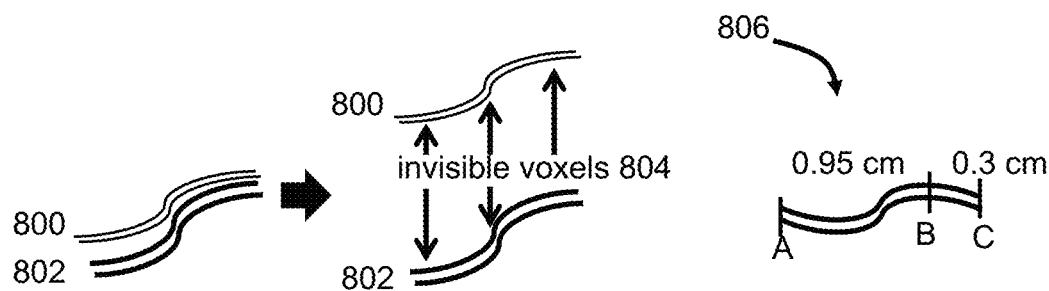
FIGS. 8A, 8B, and 8C illustrate three examples of voxel manipulation and voxel creation to separate closely spaced blood vessels or stretch blood vessels as part of the untangling of an AVM.

FIG. 8A illustrates separation of the voxels of two closely-spaced features 800, 802 via creation and insertion of invisible voxels 804. A significant limitation when viewing a complex 3D structure with multiple areas of tight overlap is the inability to visualize and assess deeper layers that are obscured. Spreading features apart can improve visualization from all angles by reducing overlap. One technique for spreading features apart is to create invisible (clear) voxels that are inserted between the features. The invisible voxels affect the voxels associated with the features, e.g. causing a change in position of one or both features.

Separation of the fragments of blood vessels may also be accomplished by applying an additive factor to the coordinates of a feature. In the illustrated example the features 800, 802 are two fragments of blood vessels. For context, the two blood vessels may have diameters of 10 voxels and be separated by 10 voxels. The top row of the top blood vessel has coordinates (99, 100, 100), (100, 100, 100), (101, 100, 100), and (102, 100, 100). The bottom row of the top blood vessel has coordinates (99, 90, 100), (100, 90, 100), (101, 90, 100), and (102, 90, 100). The top row of the bottom blood vessel has coordinates (99, 80, 100), (100, 80, 100), (101, 80, 100), and (102, 80, 100). The bottom row of the bottom blood vessel has coordinates (99, 70, 100), (100, 70, 100), (101, 70, 100) and (102, 70, 100). The coordinates of the bottom vessel may remain unchanged while an additive factor of 100 is applied to the y-values of the top vessel. The result is a shift in relative positions of the blood vessel fragments, resulting in an increase in separation at a magnitude determined by the value of the additive factor. The final coordinates of the top row of the top vessel in the illustrated example are (99, 200, 100), (100, 200, 100), (101, 200, 100), and (102, 200, 100). The final coordinates of the bottom row of the top vessel is (99, 190, 100), (100, 190, 100), (101, 190, 100) and (102, 190, 100). Invisible voxels may be created and inserted into the space created by the process.

Voxel counting metrics 806 may also be used. The voxels of a feature could be selected to have surfaces that better portray the feature. For example, the distance along the surface of blood vessel may be more accurately measured if the blood vessel is represented by cylindrical-type voxels as opposed to cuboids at even spacing. The voxel lengths along a curvilinear edge are added together to generate sub-total or total lengths. In the illustrated example, voxel counting metrics for a curvilinear distance are illustrated. Assume, for example, the length of the inferior most aspect of a straight blood vessel has coordinates (0, 0, 0), (1, 0, 0), (2, 0, 0) and (3, 0, 0); the distance of this portion of the blood vessel is 3 voxels. However, if the blood vessel is curving slightly with the length of the bottom surface of the blood vessel having coordinates of (0, 0, 0), (1, 0, 1), (2, 0, 2) and (3, 0, 3); using Pythagorean's theorem, the distance would be $3\sqrt{2}$ voxels. A key advantage the voxel counting metrics is the enhanced pre-operative planning resulting from a better understanding of the distance that a catheter needs to move within a blood vessel to reach a desired position to perform a desired task. Other counting metrics may be associated with surface areas and volumes.

Figure 8B:
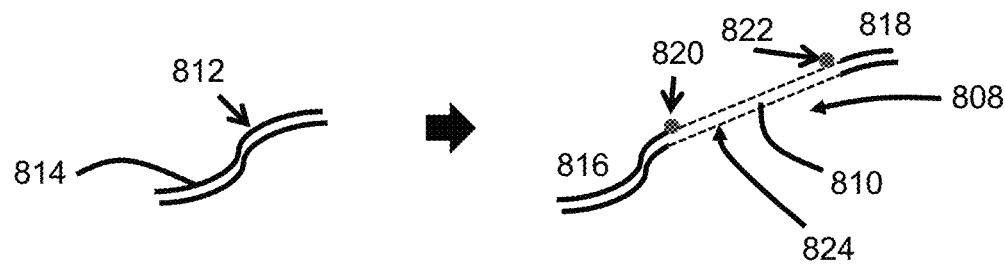

FIG. 8B illustrates tissue stretching via creation and insertion of both invisible voxels 808 and tissue-type voxels 810. Tissue stretching may help to overcome the challenge of overlapping tissues. A strategic cut point 812 on the feature 814 is selected. The feature is segmented at the strategic cut point, resulting in segments 816, 818 and stretch points 820, 822. One of the segments is pulled away from the other segment, e.g. segment 818 pulled-away from segment 816. This may be accomplished by inserting invisible voxels 808 or by applying an additive factor to the coordinates of the voxels of the segment that is being moved. To facilitate visualization of segment interconnection, computer generated lines 824 that connect the two previously contiguous, but now geographically separated, segments 816, 818 may be generated. The lines could be displayed in some enhanced fashion (e.g., false color, dashed, blinking, thin, etc.) to denote to the user which vessel is native and which vessel is computer generated. As in the previously described example, one of the segments may remain stationary while the other segment is relocated. Tissue-type voxels 810 are created and inserted to interconnect the two segments, e.g., between the lines 824 and bridging the corresponding stretch points 820, 822.

Figure 8C:
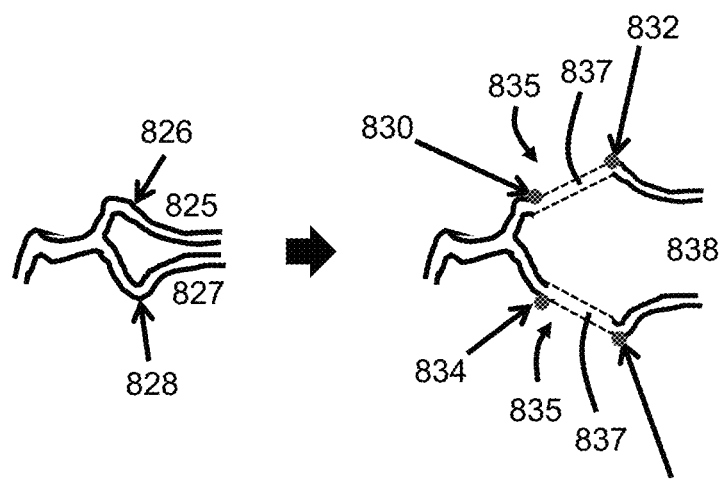

FIG. 8C illustrates use of tissue stretching to separate two closely spaced blood vessel branches 825, 827 that share a Y-shaped fork, such as commonly occurs in cerebrovascular AVMs. Strategic cut points 826, 828 from which to stretch each branch outward are selected. At each strategic cut point the corresponding branch is pulled away, e.g. by applying an additive factor. The branches may be assigned different additive factor values. Stretch points 830, 832, 834, 836 are thereby created. To help visualization of how the created segments interconnect, computer-generated lines 835 connect the two previously contiguous, but now geographically separated, segments on each branch of the natively closely spaced forked vessel. The lines could be displayed in some enhanced fashion (e.g., false color, dashed, blinking, thin, etc.) to denote to the user which segment is native and which segment is computer-generated. Tissue-type voxels 837 are created and inserted to interconnect the two segments, e.g., between the lines and bridging the corresponding stretch points. Further, invisible voxels 838 can be created and inserted to fill the void between the newly geographically separated segments. Thus, a user can effectively pull-apart a complex structure (e.g., cerebral AVM) such that the tangle and connections can be better visualized and understood.

Figure 9:
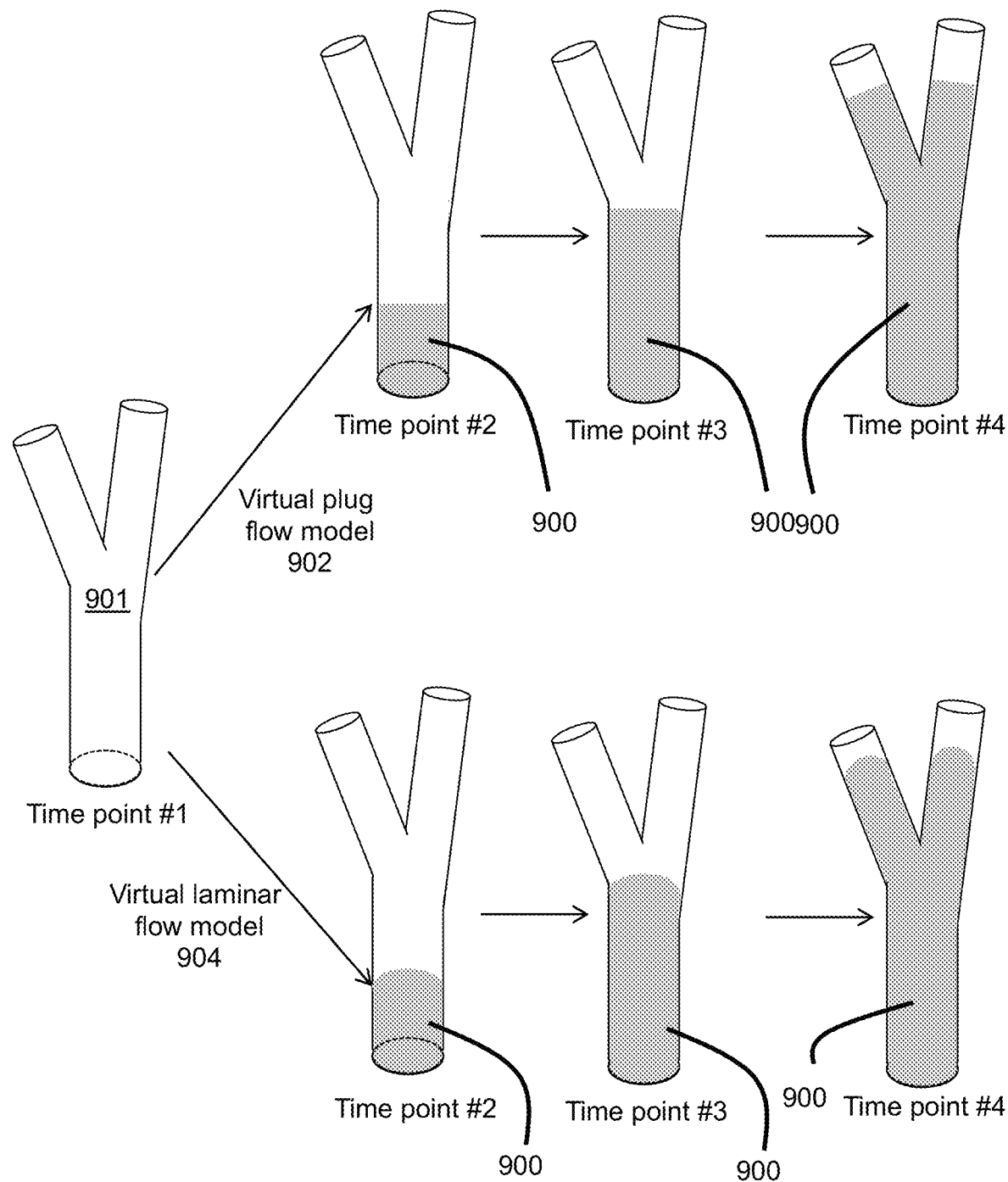
FIG. 9 illustrates examples of insertion of dynamic-type voxels, which in the illustrated example is virtual contrast flowing in a tubular shaped blood vessel with plug flow and laminar flow models.

FIG. 9 illustrates insertion of dynamic-type voxels 900 to represent virtual contrast flowing in an artery 901 with plug flow 902 and laminar flow 904 models. Typically, this injection would occur in an artery, but would not necessarily be restricted to the artery. It could also be performed in a vein or even GI track lumen. At time point #1, there is no virtual contrast within the artery. At time points #2, #3, and #4, the virtual contrast progressively fills in from proximal to distal. The virtual laminar flow model 904 has faster flow in the center of the artery as compared to the lumen closest to the wall. A wide variety of other flow models can be implemented, such as accounting for normal blood vessels or diseased blood vessels (e.g., stenosis due to atherosclerosis).

Figure 10:
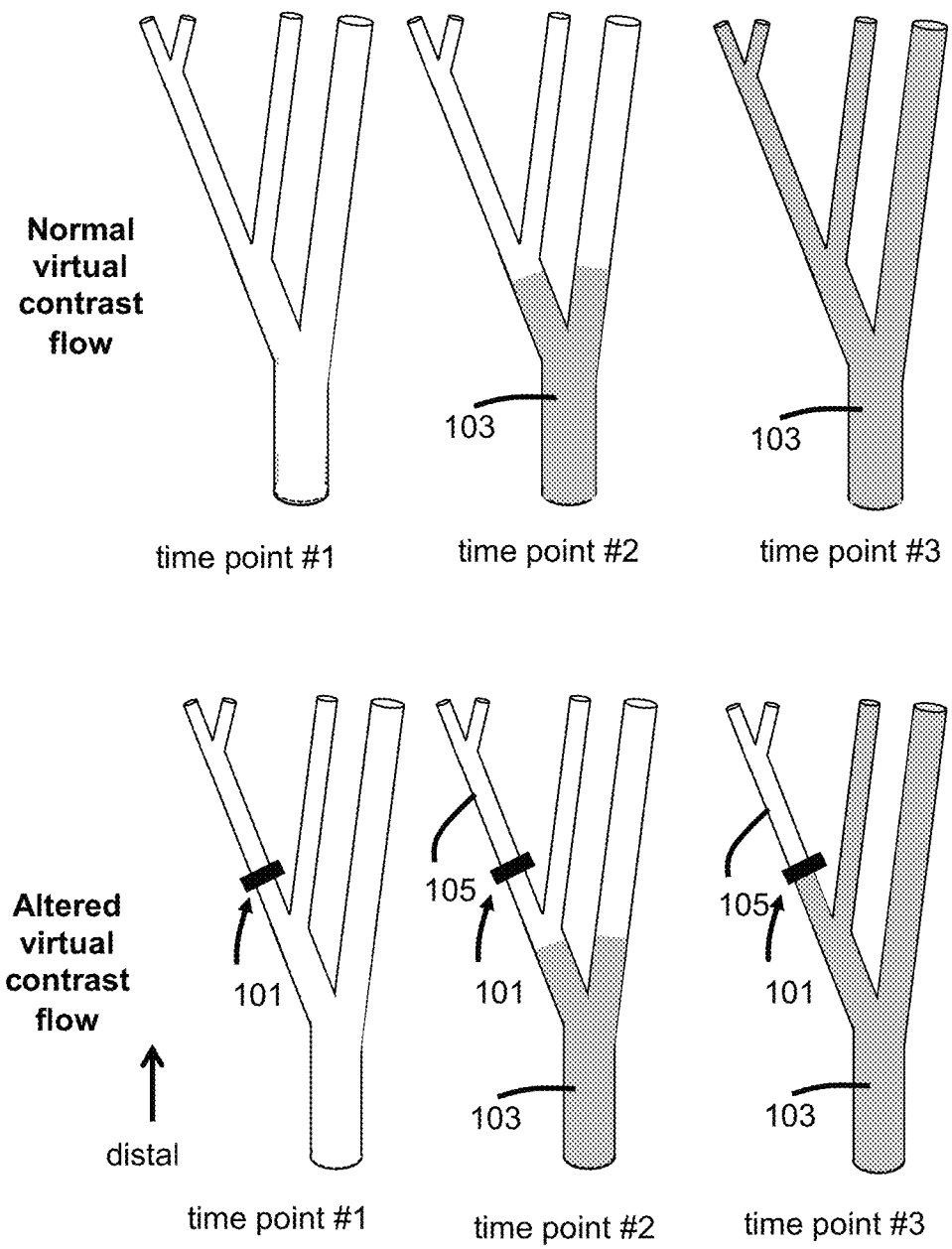
FIG. 10 illustrates the altered virtual contrast flow through the placement of an interactive voxel called a virtual occluder.

FIG. 10 illustrates altered virtual contrast flow resulting from placement of an interactive voxel 101 such as a virtual occluder. For comparison, both normal virtual contrast flow and altered virtual contrast flow with placement of a virtual occlude are shown. The virtual contrast 103 can progress from proximal to distal in the virtually occluded branch 105 up to the point of the virtual occluder, but not beyond the virtual occluder. Insertion of virtual contrast is not impeded in the non-occluded branches. Thus, the insertion of an interactive voxel, such as a virtual occluder, can simulate placement of a surgical clip.

Figure 11:
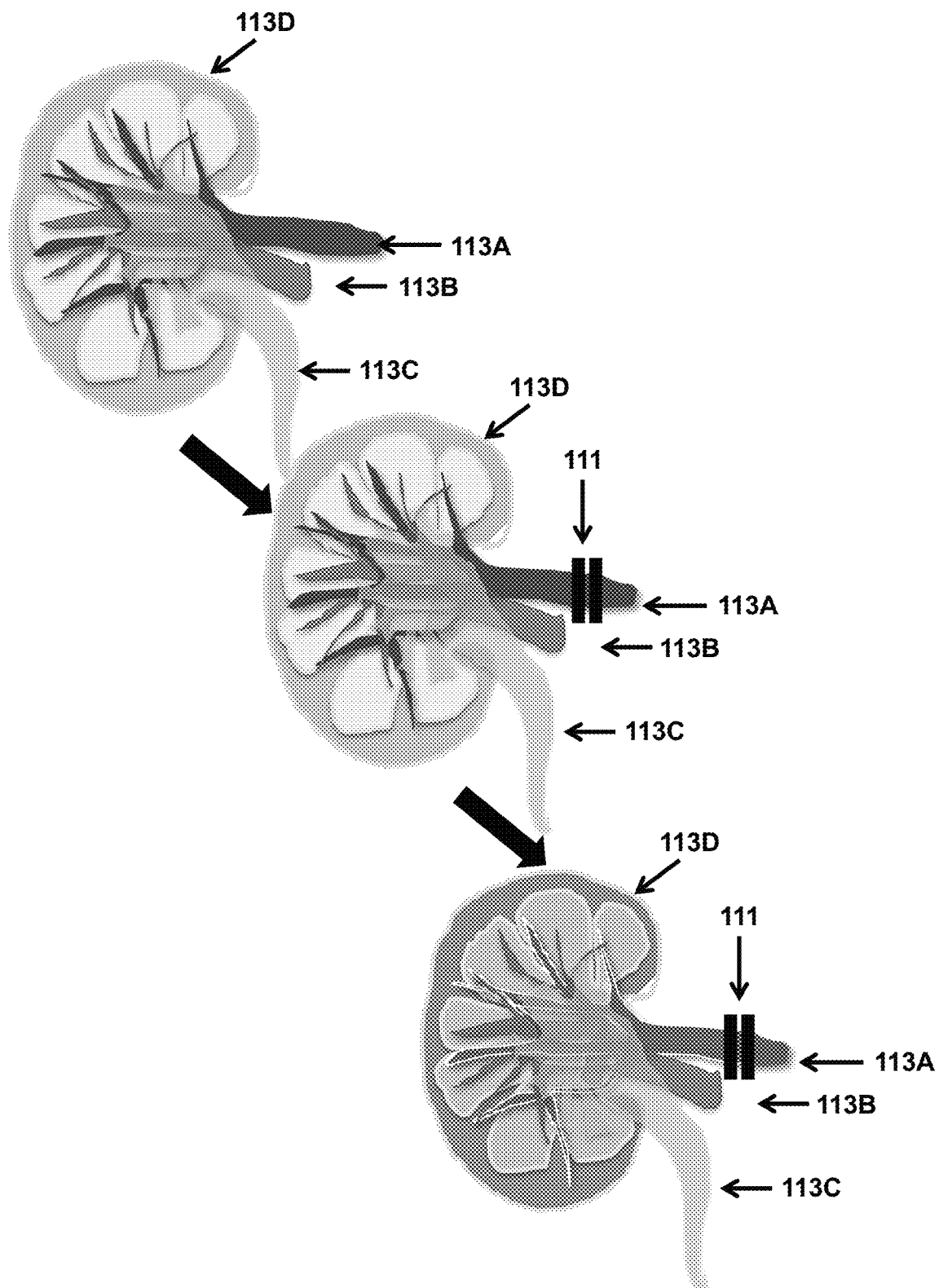
FIG. 11 illustrates an example of voxel manipulations (e.g., ischemic appearance of kidney) in relation to placement of interactive-voxels (e.g., virtual occluder placed over the renal artery).

FIG. 11 illustrates automatic voxel manipulations in response to placement of interactive-voxels. In the illustrated example the ischemic representation of a kidney changes in response to placement of virtual occluders 111 over the renal artery 113A. 113B illustrates the renal vein. 113C illustrates the ureter. The kidney changes from the normal pink color to blue as the blood supply is cut off. Voxel alteration to reflect pathologic process of renal ischemia. In some embodiments, a simulation of physiology is performed. Some embodiments comprise simulating physiology in an imaging examination comprising: using a three-dimensional dataset of a portion of a body wherein said portion of said body contains said body tissues, wherein said three-dimensional dataset is comprised of voxels, wherein said voxels correspond to said body tissues, and wherein voxels in said three-dimensional dataset have numerical values; modifying voxels of said three-dimensional dataset to generate a simulated physiologic change of said body tissues comprising: wherein said modifying voxels of said three-dimensional dataset comprises altering numerical values of voxels corresponding to body tissues of said three-dimensional dataset, wherein said altering said numerical values of voxels corresponding to body tissues of said three-dimensional dataset is performed in accordance with said simulated physiologic change of said body tissues, wherein said modifying voxels of said three-dimensional dataset creates an appearance of said simulated physiologic change; and displaying said modified three-dimensional dataset to a user. In some embodiments, voxel alteration may be performed to mimic a physiologic change or pathologic change or a structure. An artificial intelligence algorithm can be utilized in this process. Examples of physiologic change include, but are not limited to the following: blood flow alterations to body tissue; body tissue responses to medications; body tissue responses to radiation; body tissue responses to surgery; and, body tissue changes over time due to age. Examples of pathologic change include, but are not limited to the following: new, growing, shrinking or resolved tumors; new, worsening, healing or healed traumatic injuries such as fractures; new, worsening, resolving or resolved infections, inflammatory disease, neurological disease, cardiovascular disease, endocrine disease, metabolic disease, gastrointestinal disease, or other diseases of the human body. Some embodiments comprise additional modifications of numerical values of voxels of said modified three-dimensional dataset to generate a second modified three-dimensional dataset wherein said second modified three-dimensional dataset simulates a different time point. Note that this process can also be performed for veterinarian medicine. More specifically, the kidney slightly decreases in size and changes in color (or grayscale based on user preferences). Voxel manipulation to reflect expected changes in blood flow after the interactive virtual occluder is placed. The voxels of the kidney parenchyma are interactive-type voxels that are pink when well perfused but change to blue when the blood supply is cut off by the virtual occluder. Virtual representation of such a procedure might be implemented where an individual is undergoing a nephrectomy for renal transplant or renal cell carcinoma. It is anticipated that the insertion of interactive voxels will aid in diagnostic accuracy and surgical planning.

Figure 12:
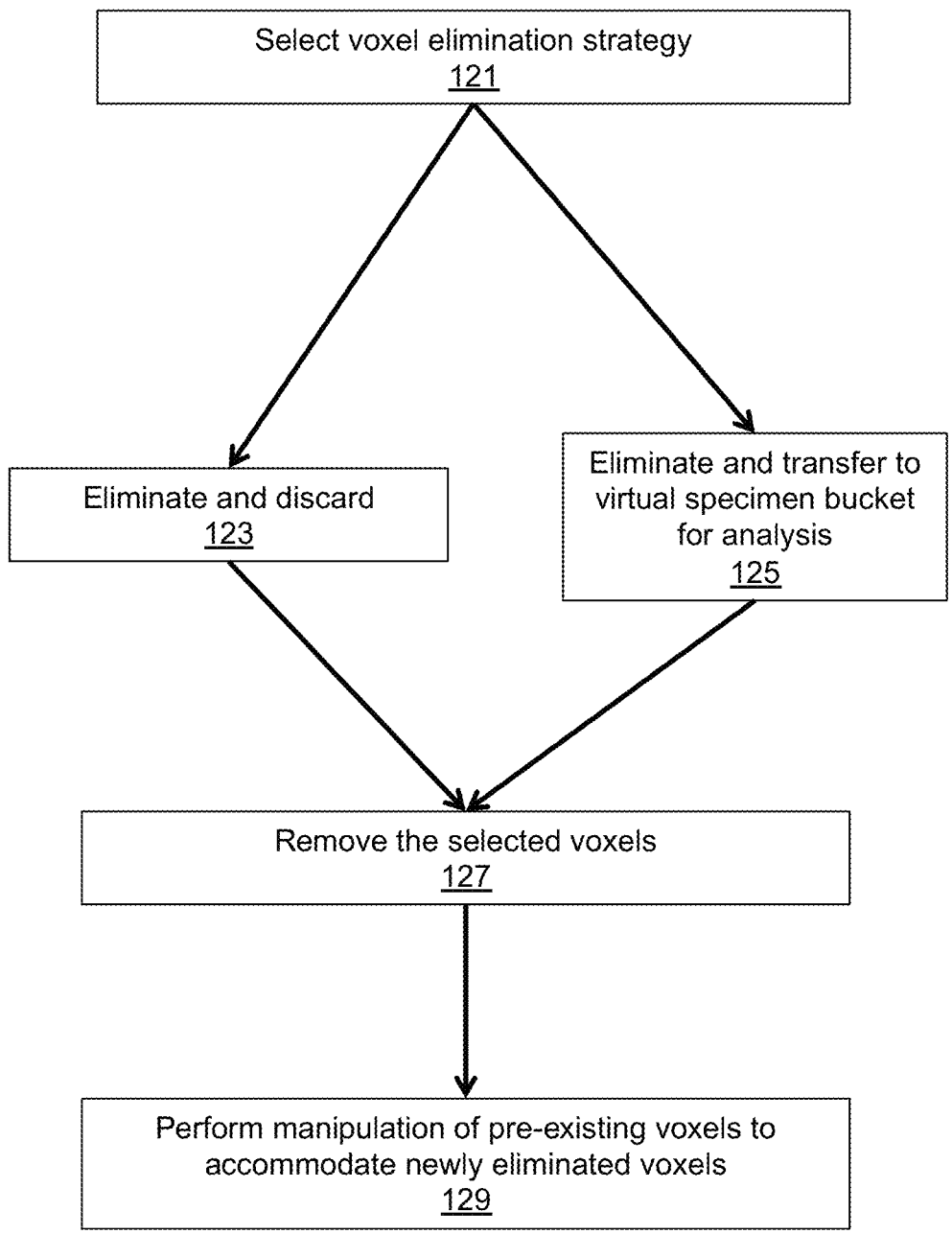
FIG. 12 is a flow diagram that illustrates voxel elimination in greater detail, including volumetric-type elimination, surface-type elimination, discarding eliminated voxels, and placing eliminated voxels into a virtual specimen bucket for analysis.

FIG. 12 illustrates voxel elimination. Step 121 is to select a voxel elimination strategy type. Examples include volumetric-type elimination and surface-type elimination. A volumetric-type elimination can be performed using a 3D cursor such as that described in U.S. Pat. No. 9,980,691 to select a volume. An example of this would be to place the volume-subtending 3D cursor over the area of interest and subtract all voxels outside (or inside) the volume. Surface-type elimination removes a single-voxel deep layer of the whole surface, which would allow analysis of a tumor or ablate away areas of non-interest that are in the way. Alternatively, the insertion of a virtual object could override (and replace) native voxels for elimination. The process may be guided through placement of strategic elimination points and strategic non-elimination points. Eliminated voxels can be either discarded as shown in step 123 or placed into a virtual specimen bucket for analysis as shown in step 125. After the elimination and removal of voxels as indicated in step 127, manipulation of the pre-existing voxels (i.e., those in place prior to the elimination) could be performed to fill the void created as indicated in step 129.

Figure 13:
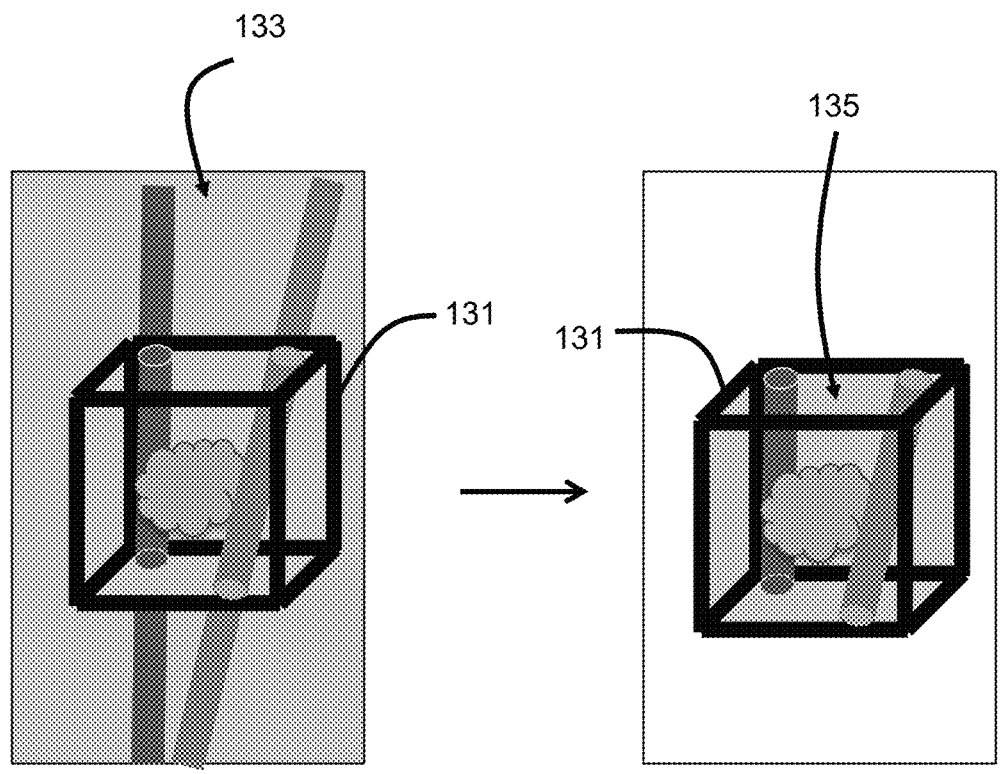
FIG. 13 illustrates volumetric-type voxel elimination using a 3D cursor where voxels outside of the 3D cursor are eliminated and voxels inside of the 3D cursor are retained.

FIG. 13 illustrates an example of voxel elimination via volumetric-type elimination with use of a 3D cursor 131. Voxels 133 located outside of the volume defined by the 3D cursor are eliminated. Voxels 135 located inside of the volume defined by the 3D cursor are retained. This voxel elimination technique may be used to isolate an area of interest, such as a tumor and the immediately surrounding anatomy.

Figure 14:
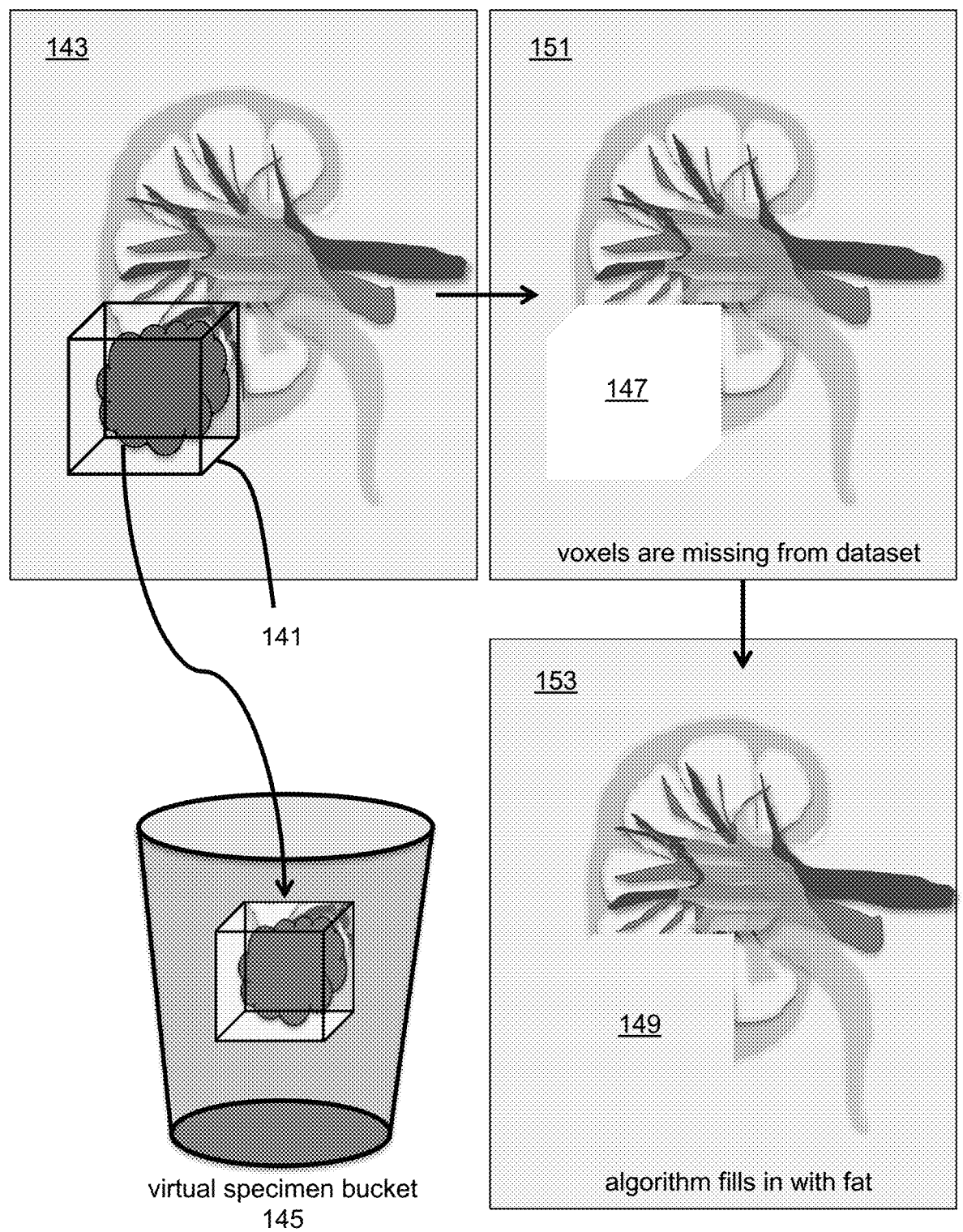
FIG. 14 illustrates voxel elimination via a volumetric-type elimination with the use of a 3D cursor where voxels inside of the 3D cursor are placed into a virtual specimen container and the void is filled in by coordinated multi-voxel shift of nearby voxels.

FIG. 14 illustrates voxel elimination via a volumetric-type elimination with the use of a 3D cursor 141. Voxels located inside of the 3D cursor in image 143 are placed into a virtual specimen container 145. The void 147 resulting from voxel elimination, as shown in image 151, is filled in by coordinated multi-voxel shift of nearby voxels 149, as shown in image 153. The virtual specimen container can be used for many purposes. If the structure is unknown, it can be analyzed pre-operatively in comparison with other similar tissues in an attempt to refine the differential diagnosis, so that the medical team would be more confident. After getting a definitive diagnosis via pathology, the object could be labeled and added to a training database for machine learning purposes. After the object is removed, an option would be for manipulation of local voxels, such as filling in with the adjacent fat tissue.

Figure 15A:
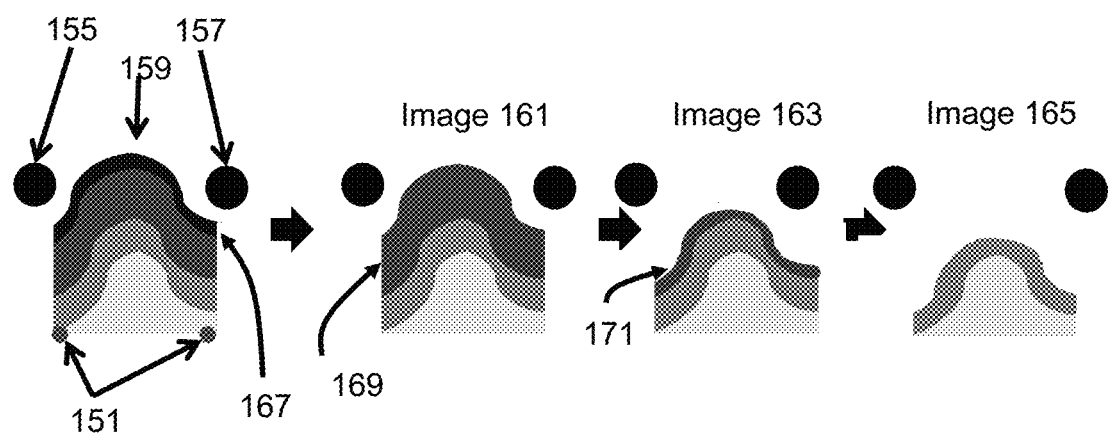
FIGS. 15A and 15B illustrate voxel elimination via a multi-step surface-type layer-by-layer approach, either via a portion of a surface at a time or a whole layer of the whole surface one voxel layer at a time.

FIG. 15A illustrates virtual ablation of a portion of a layer of the surface of a gyrus 159 of brain using voxel elimination via a multi-step surface-type layer-by-layer approach. This may be useful where the gyrus is disposed between blood vessels 155, 157. Strategic elimination points 151 (or strategic elimination voxels) are designated in initial image 153. These points can be placed underneath the desired ablation surface to guide the direction of the surface ablation. Voxels are removed, layer-by-layer, in a directed fashion, such that smaller and smaller surface shells of a structure are generated as shown in progression by images 161, 163, and 165. Image 161 illustrates the outer most shell of gyrus ablated improving visualization of the vessels. Image 163 illustrates the next shell of gyrus ablated improving visualization of the vessels. Image 165 illustrates the gyrus of brain obscures visualization of the vessels. Initially, a row 167 of the top layer of the cortex may have voxels (100, 100, 100), (101, 100, 100), (102, 100, 100) and (103, 100, 100). Upon removal of this top layer of cortex, the new top row 169 would then be (100, 99, 100), (101, 99, 100), (102, 99, 102) and (103, 99, 100). Upon removal of that layer of cortex, the next highest row 171 would be (100, 98, 100), (101, 98, 100), (102, 98, 102) and (103, 98, 100). The eliminated voxels are removed from the displayed volume.

Figure 15B:
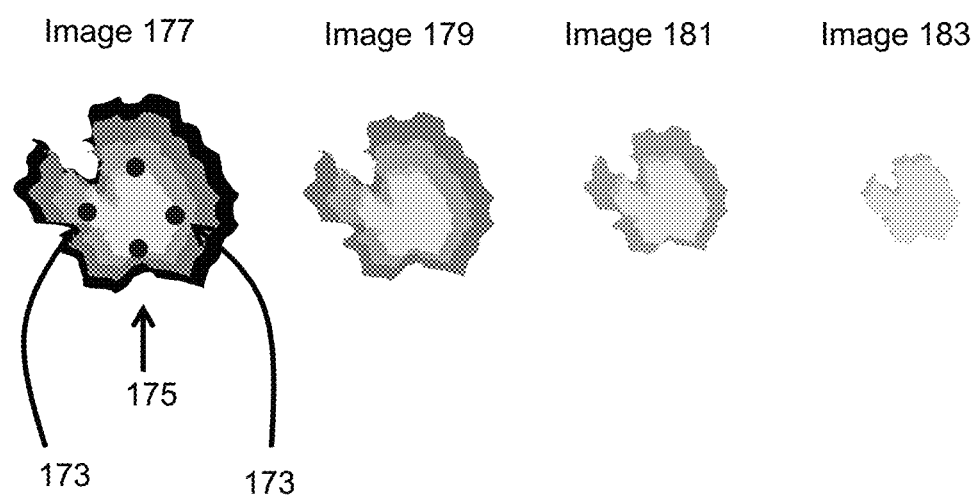

FIG. 15B illustrates virtual ablation of a whole layer of the surface of a mass 175 using strategic non-elimination points 173 (or strategic non-elimination voxels). These can be placed within the desired structure that will be ablated to designate the no further ablation zone. Images 179, 181, and 183 illustrate virtual ablation of shells from outer to inner relative to pre-ablation image 177. Image 179 illustrates the outer most shell of the mass ablated. Image 181 illustrates the next shell of the mass ablated. Image 183 illustrates the next shell of the mass ablated. Uses for surface-type layer-by-layer ablation may include, but are not limited to, the following: removing a portion of an object of non-interest while preserving some of it for context; simulating the effects of chemotherapy; simulating the effects of radiation therapy; and, viewing the inside of a tumor in a layer-by-layer fashion. Some of the structures are less responsive to chemotherapy and these regions could be assigned a voxel property designated as more difficult to ablate.

FIGS. 16A, 16B, 16C, and 16D illustrate specific examples of virtual insertion into 3D medical imaging datasets where distortion of the adjacent tissues is not performed. The examples include radiofrequency ablation of a renal mass, coiling of an aneurysm, placement of femoral neck screws, and comparing a breast mass over multiple time points, each of which is simulated using the techniques described above.

Figure 16A:
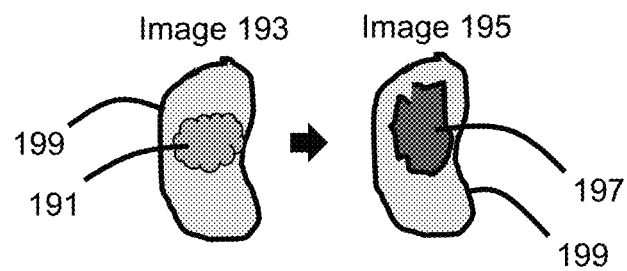
FIGS. 16A, 16B, 16C and 16D illustrate the insertion into 3D medical imaging datasets where distortion of the adjacent tissues is not performed with four examples including radiofrequency ablation of a renal mass, coiling of an aneurysm, placement of femoral neck screws or comparing a breast mass over multiple time points.

FIG. 16A illustrates a renal mass 191, for which a treatment called radiofrequency ablation can be performed. The radiofrequency ablation treatment is simulated by inserting a virtual ablation zone in image 193 using techniques described above. Image 195 shows a computer-generated 3D digital object 197 that is placed within the kidney 199, replacing voxels that correspond to the mass 191 and that correspond to some normal kidney tissue. Insertion includes only the replacement of normal kidney voxels and kidney mass voxels with virtual ablation zone voxels. No adjacent voxels (or tissues) are distorted.

Figure 16B:
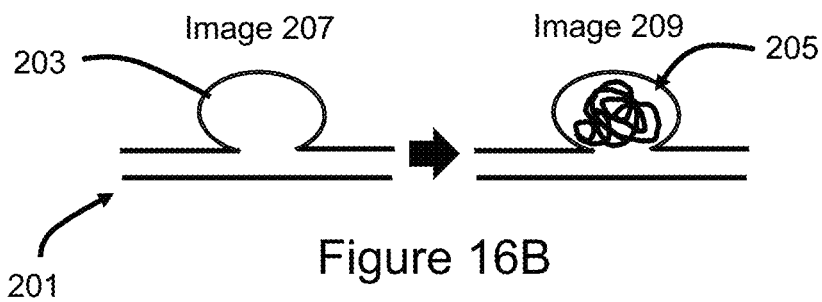

FIG. 16B illustrates a blood vessel 201 with an aneurysm 203, for which a treatment called endovascular coiling can be performed. The endovascular coiling is simulated by inserting a virtual coil 205 into the aneurysm 203 in image 207 using techniques described above. Resulting image 209 shows the virtual coil as a computer-generated 3D digital object that is placed within the aneurysm replacing voxels that correspond to the blood inside the aneurysm sac. The insertion includes only the replacement of blood voxels with virtual coil mass voxel. No adjacent voxels (or tissues) have been distorted.

Figure 16C:
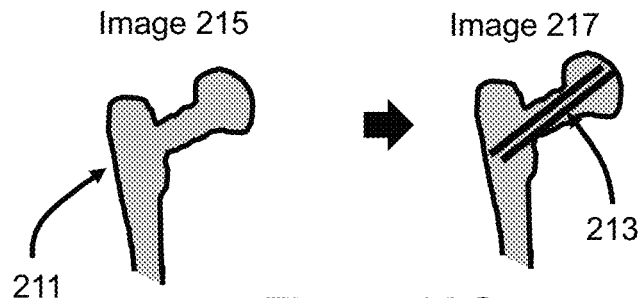

FIG. 16C illustrates a femur 211, for which placement of a femoral prosthesis can be performed in the event that the femur is fractured. The procedure is simulated by inserting virtual femoral neck fixation hardware 213 in image 215. Resulting image 217 shows the hardware as a computer-generated 3D digital object that is placed within the femur and replaces other voxels such as bone or bone marrow. The insertion includes only the replacement of cortical bone voxels and bone marrow voxels with virtual femoral neck fixation voxels. No adjacent voxels (or tissues) have been distorted.

Figure 16D:
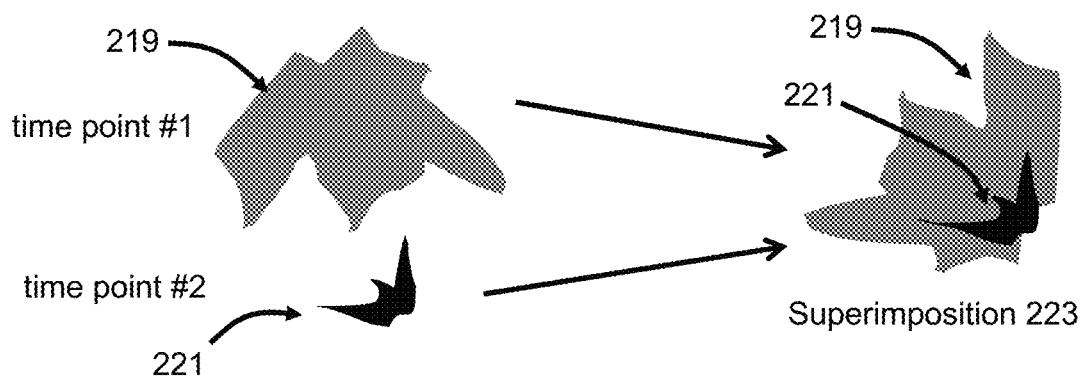

FIG. 16D illustrates superimposition 223 of temporal versions 219, 221 of a segmented-out breast mass taken at different points in time. The breast is a mobile structure and can change positions, but can also change in configuration (e.g., flatten, etc). Because of this, accurate comparison of the mass at two points in time is difficult to represent. To properly register and compare the two temporal versions 219, 221 of the mass, one or both of the temporal versions may need to be rotated and/or deformed (since the breast is a soft tissue). Performing deformation of the breast masses such that they are superimposed, have the same orientation, and are deformed the same way using the techniques described above may prove to help improve comparison of how the breast mass changes over time. Note that the superimposition represents the same mass at different time points when it is different sizes. Proper registration of the masses is essential in order for precise comparison of the size, speculations, margins, involvement of adjacent structures, etc. Thus, rotation, translation, and deformation of the masses may be required to achieve best comparison.

Figure 17:
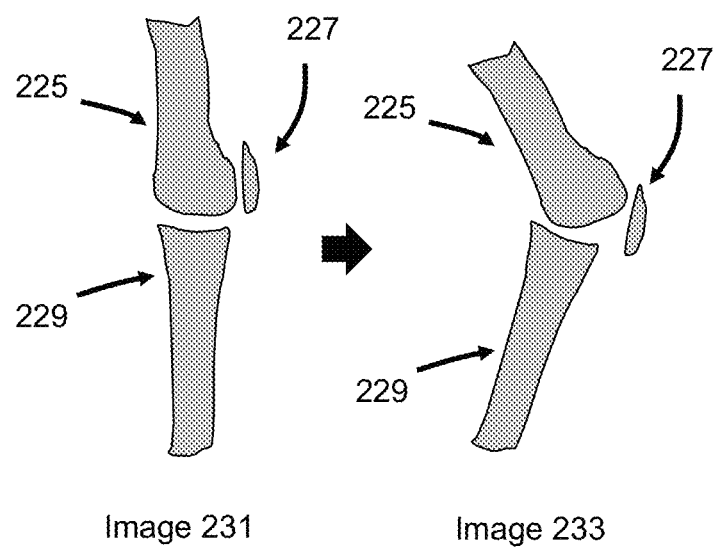
FIG. 17 illustrates coordinated multi-voxel manipulation to achieve virtual motion of anatomic structures within 3D medical imaging datasets, such as motion at the knee joint.

FIG. 17 illustrates coordinated multi-voxel manipulation to achieve virtual motion of anatomic structures within 3D medical imaging datasets. Virtual motion is implemented by allocating tissue properties to each tissue within a volume and simulating movement of at least one anatomic structure. The anatomic structure in the illustrated example is a knee joint. Image shows three bones (femur 225, patella 227, tibia 229) at the knee joint. By assigning each voxel in these bones a rigid-type tissue property, motion at the knee joint can be modeled and translated in position via a coordinated multi-voxel shift using the techniques described above. All three bones shift in orientation and position from image 231 to image 233. This requires a coordinated multi-voxel shift. For simplicity, soft tissues are not shown. Note that no voxels are eliminated or created. Voxels are only manipulated. The bones have rigid-type properties and therefore would be non-deformable if pushed upon. However, since the bones meet at a joint, virtual range of motion can be performed. The virtual motion can be viewed in 3D using augmented reality headset, e.g. as described in U.S. Pat. No. 8,384,771.

Figure 18:
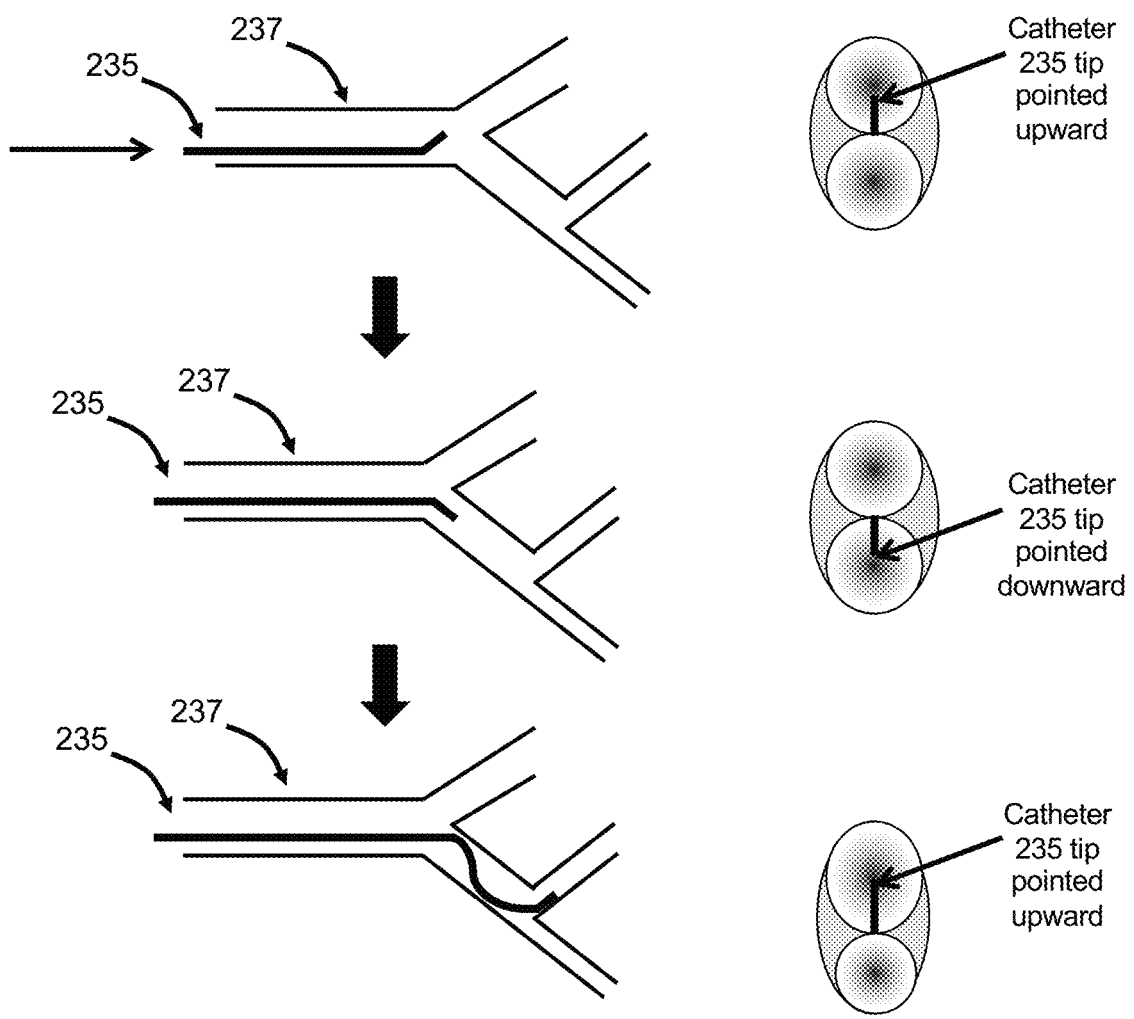
FIG. 18 illustrates coordinated multi-voxel manipulation to achieve virtual motion of virtual objects inserted into 3D medical imaging datasets, such as a motion of a virtual catheter inside of a blood vessel with tunnel view shown.

FIG. 18 illustrates coordinated multi-voxel manipulation to achieve virtual motion of virtual objects inserted into 3D medical imaging datasets. The specifically illustrated example is motion of a virtual catheter 235 inside of a blood vessel 237, rendered in both side view 239 and tunnel view 241 at three different points in time. This example illustrates use of voxel manipulation to represent real-time movement of anatomic structures or virtual objects within a 3D medical imaging dataset. The virtual surgical object can take on many forms, one of which is a vascular catheter. The virtual object, e.g. virtual catheter, is assigned physical properties (e.g., hardness, malleability, etc.), in a manner like that of tissues as already described above. Thus, when the soft virtual catheter is pushed through the blood vessel, the virtual catheter deforms when it is pressed against a more rigid blood vessel.

The tip of the virtual catheter 235 is bent, which enables efficient navigation through the branches of the blood vessel. Assume, for example, that the first several coordinates of the top row of a blood vessel 237 of diameter of 20 voxels were (100, 100, 100), (101, 100, 100), (102, 100, 100), (103, 100, 100), (104, 100, 100), and (105, 100, 100). And, assume that the first several coordinates of the bottom row of that blood vessel were (100, 80, 100), (101, 80, 100), (102, 80, 100), (103, 80, 100), (104, 80, 100) and (105, 80, 100). The distal portion of a vascular catheter commonly used to track along the inside of a blood vessel could take on the coordinates (100, 90, 100), (101, 90, 100), (102, 90, 100), (103, 91, 100), and (104, 92, 104). If the catheter is advanced one voxel in the x-direction to reach an x-coordinate of 105, it would take on the coordinates (100, 90, 100), (101, 90, 100), (102, 90, 100), (103, 90, 100), (104, 91, 104), and (105, 92, 100). The bent tip of the catheter accounts for the deviation in the y-direction. Because the material inside the vessel is liquid blood, the material is free to move and remaining tissues will not need to undergo virtual tissue deformation. The tunnel view 241 can be from the perspective of the distal catheter looking forward from the long portion of the catheter connected to the tip. The catheter tip and the upcoming vascular branches can serve to aid in both the navigation process and the understanding of the vascular lumen.

Figure 19:
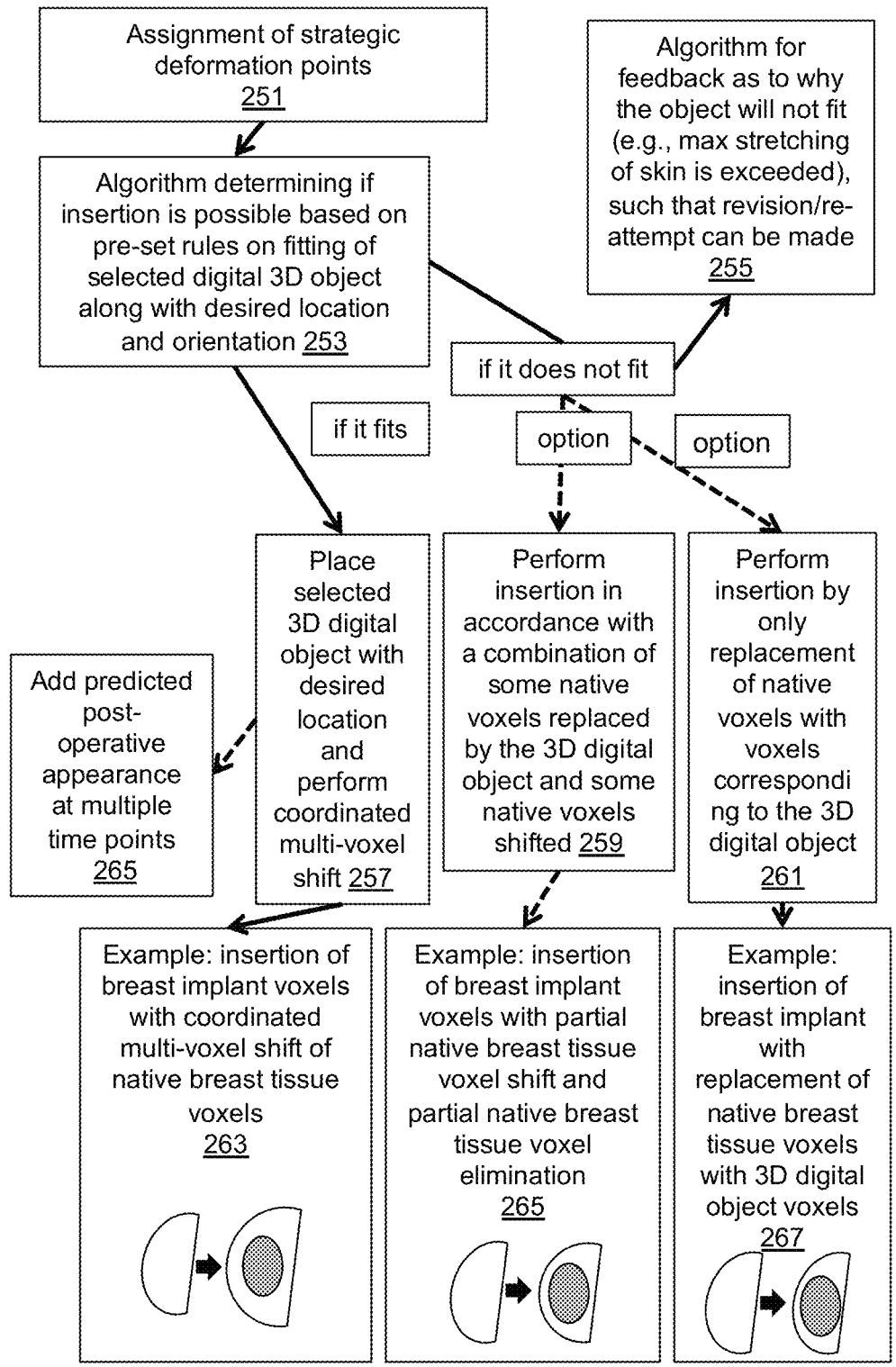
FIG. 19 is a flow diagram that illustrates a fitting algorithm and strategic deformation points, which can be used for placement of a virtual object into a 3D medical imaging dataset.

FIG. 19 is a flow diagram that illustrates a fitting algorithm and strategic deformation points that can be used for placement of a virtual object into a 3D medical imaging dataset. After tissue-type voxels and virtual surgical object-type voxels are assigned tissue properties, and strategic deformation points are assigned, as indicated in step 251, the user specifies the desired placement location and surgical path by which the placement occurs. The algorithm determines if the placement is possible as indicated in step 253. Object placement may be performed via one of three options: coordinated multi-voxel shift of native tissue voxels 257; partial replacement of native voxels and partial coordinated multi-voxel shift of native voxels 259; and complete replacement of native breast tissue voxels with 3D digital object voxels 261. It is important in at least some implementations to have the interactive component of use of the strategic deformation points to achieve desired fitting. Step 257 may be selected in the case where the preset fitting rules are satisfied. An example 263 is insertion of breast implant voxels with coordinated multi-voxel shift of native breast tissue voxels. An option 265 is to add predicted post-operative appearance at multiple time points (e.g., edema seen at 1-day post-op, but not at 1-year post-op). In the case where the preset fitting rules are not satisfied the algorithm provides feedback to the user as indicated in step 255. Steps 259 and 261 are options in that case. An example 265 in which step 259 is selected is insertion of breast implant voxels with partial native breast tissue voxel shift and partial native breast tissue voxel elimination. An example 267 in which step 261 is selected is insertion of breast implant with replacement of native breast tissue voxels with 3D digital object voxels.

Figure 20:
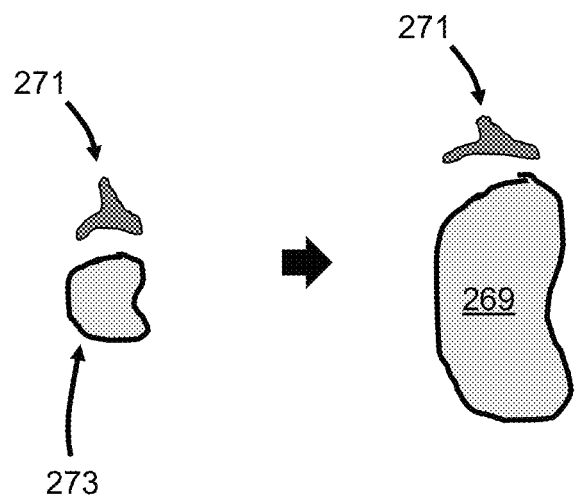
FIG. 20 illustrates an example of deformable tissues where a 3D digital object is inserted into volumetric medical images and there is partial native voxel manipulation and partial native voxel elimination.

FIG. 20 illustrates an example of virtual deformable tissues where a 3D digital object is inserted into volumetric medical images and there is partial native voxel manipulation and partial native voxel elimination. The specifically illustrated example is insertion of virtual renal transplant. The insertion includes the addition of voxels from another patient's 3D medical imaging exam (from the donor kidney 269) onto the current patient's 3D medical imaging exam (the recipient of the renal transplant); note that the larger donor kidney distorts the appearance of the recipient's native adrenal gland 271 located above the recipient kidney 273, which is achieved through a coordinated multi-voxel shift.

Figure 21:
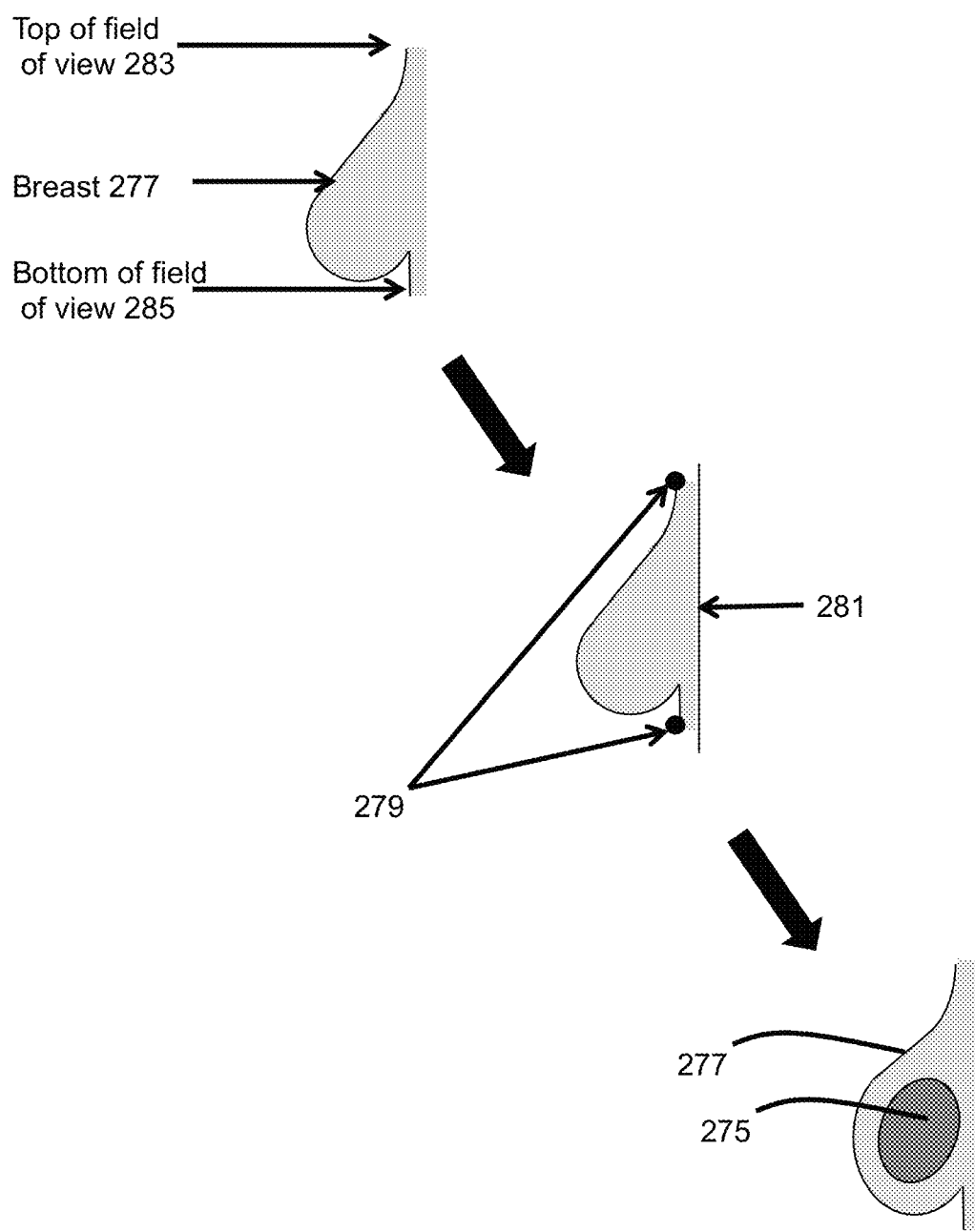
FIG. 21 illustrates an example of the use of deformable tissues and strategic deformation points, such as placement of a breast implant into the breast.

FIG. 21 illustrates an example of the use of deformable tissues and strategic deformation limiting features to simulate placement of a breast implant 275 into the breast 277. The strategic deformation limiting features help guide the insertion process. In this example, strategic deformation points 279 are placed near the top and bottom of the field of view 283, 285, and a strategic deformation line 281 is placed at the back of the breast where the ribs are located. Such strategic deformation limiting features help set maximum shift values and are helpful at the edge of the field of view. The strategic deformation points may be assigned a 1 cm maximum motion limit, and the strategic deformation line may be assigned a 1 mm maximum motion limit, for example, and without limitation. Note that although the strategic deformation limiting features have minimal to no shift, the remainder of the breast undergoes a coordinated multi-voxel breast tissue shift during placement of the 3D digital representation of the breast implant 275. Maximum motion limits may be assigned to other points at the edge of the field of view. For example, in an MRI of the breast, the user can insert a strategic minimal deformation point at the skin below the breast at the inferior most aspect of the field of view and then select for the maximum amount of shift that this point can be stretched.

Figure 22:
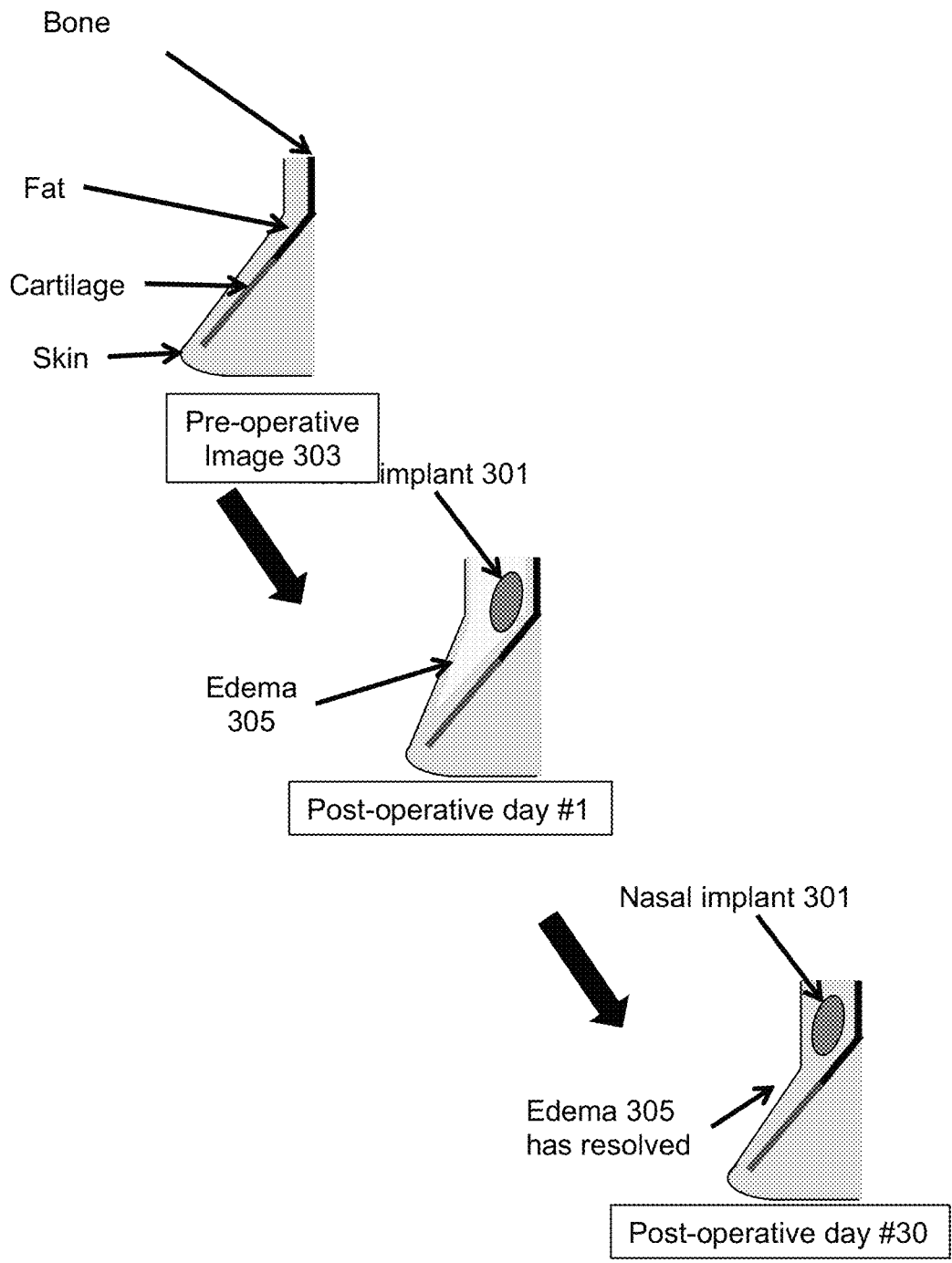
FIG. 22 illustrates an example of deformable tissues showing virtual expected post-operative appearance with change over time, such as placement of a nasal implant.

FIG. 22 illustrates use of virtual deformable tissues to simulate expected post-operative appearance with change over time. The specifically illustrated example is placement of a nasal implant 301. The simulation is achieved by creating and inserting both fixed-type and dynamic-type voxels in a pre-operative image 303. Specifically, the edema 305 is represented by a dynamic-type voxel, which is present on the simulated post-operative day #1, but resolves completely by the simulated post-operative day #30. Alternatively, virtual disappearance can be performed (e.g., certain tissues, such as fat-graft placements are known to shrink over time; other conditions such as edema in the soft tissues, volume overload in the vasculature are also known to be temporary and can undergo part or total disappearance over time).

Figure 23:
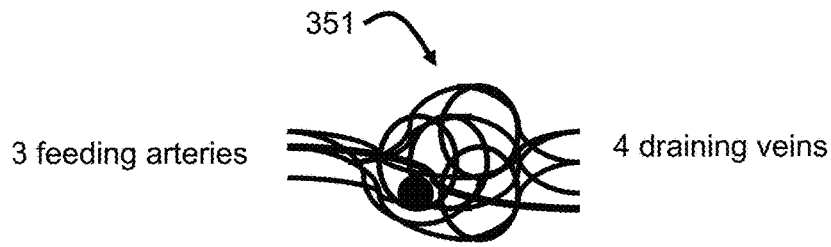
FIG. 23 illustrates a flow diagram for the use of voxel manipulation strategies to improve understanding of complex 3D anatomy, such as a cerebral arteriovenous malformation (AVM).
Figure 23:
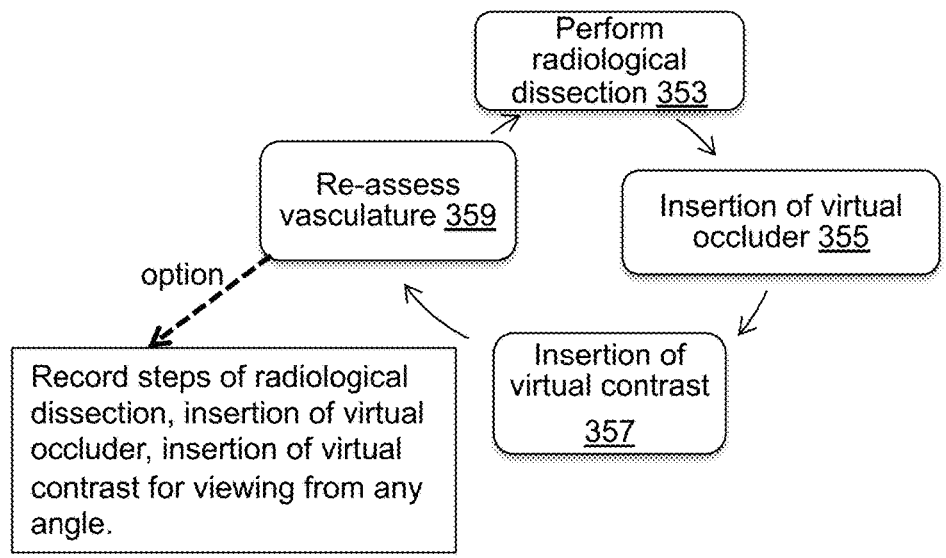
Figure 23:
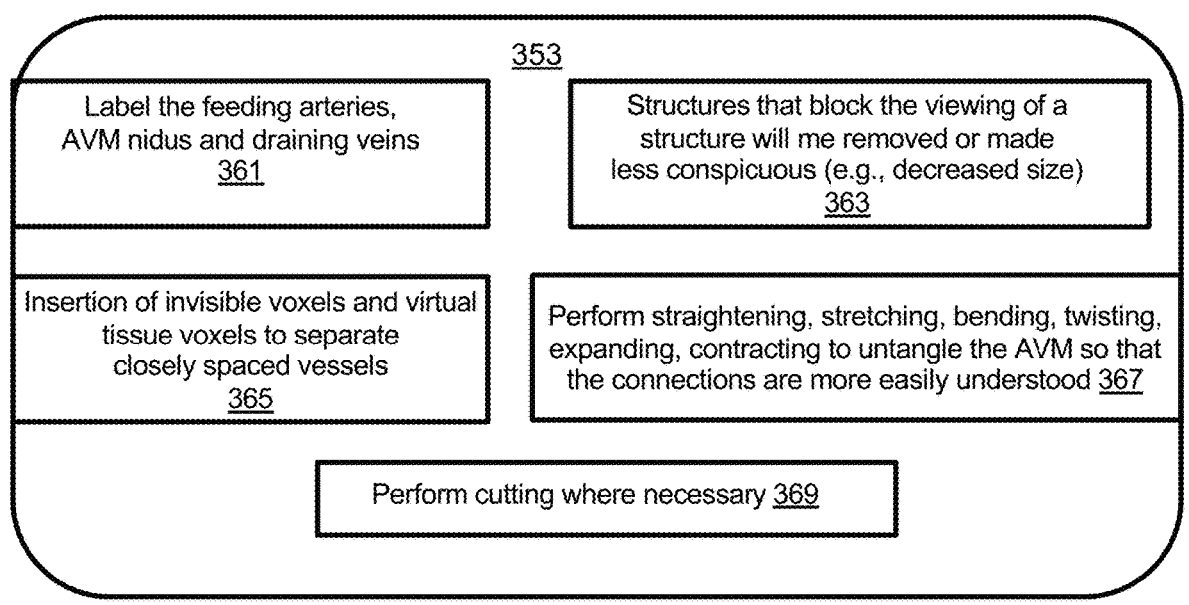

FIG. 23 illustrates use of voxel manipulation processes to improve understanding of complex 3D anatomy. The specifically illustrated example is a cerebral arteriovenous malformation (AVM) 351. Multiple aspects described above are used to facilitate pre-operative planning, including determining how to best treat the cerebrovascular AVM. The example AVM is characterized by three feeding arteries, a complex tangle of blood vessels, an intranidal aneurysm within the tangle (black circle) and four draining veins. It is difficult to understand from an unprocessed image how each of the branches of the AVM connect. Treatment options include open surgical resection including clip placement over certain blood vessels or endovascular embolization. A virtual radiological dissection 353 is performed to improve understanding of the complex 3D anatomy. A virtual occluder is then inserted as shown in step 355, followed by insertion of virtual contrast as shown in step 357. The vasculature is then re-assessed as indicated in step 359. The steps may be iterated, and optionally recorded.

The virtual radiological dissection step 353 may include a variety of sub-steps to untangle the complex structure of the AVM such that each of the branches can be better understood. For example, the feeding arteries, AVM nidus and draining veins may be labelled as indicated in sub-step 361. Viewing may be enhanced or optimized with filtering, segmentation, 3D cursor use, 3D headset viewing. Any structures that block the viewing may be ablated or deformed to minimize obscuration of the AVM as indicated in sub-step 363. Creation and insertion of invisible-type voxels and tissue-type voxels connects the previously contiguous, but now separated structures as indicated in sub-step 365. Next, a series of untangling processes possibly including one or more of straightening, stretching, bending, and twisting are performed as indicated in sub-step 367. Virtual cutting may be performed as indicated in sub-step 369.

A variety of features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

Figure 24:
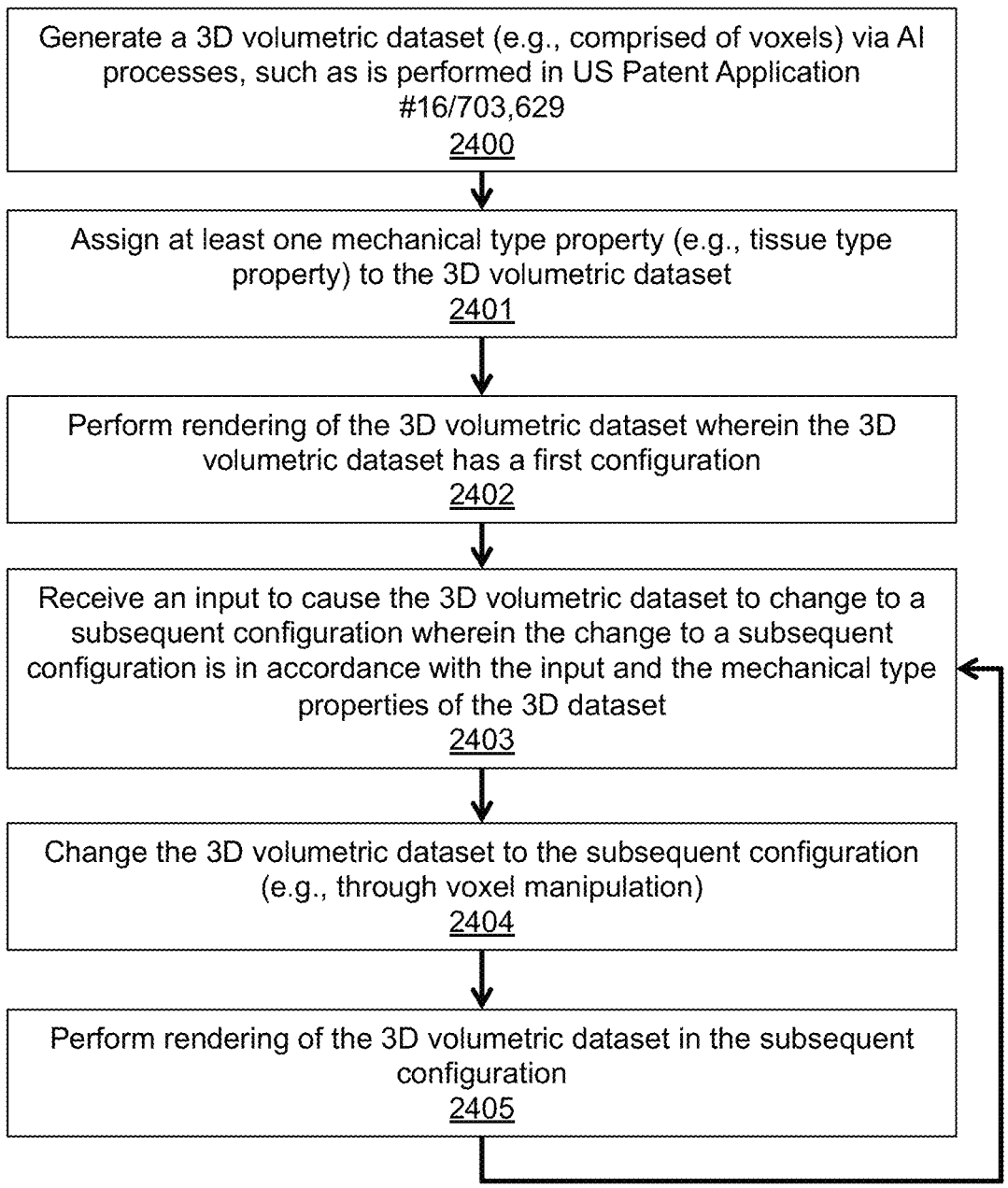
FIG. 24 illustrates a method for generating a 3D volumetric dataset through artificial intelligence processes and then performing altering the 3D volumetric dataset.

FIG. 24 illustrates a method for generating a 3D volumetric dataset through artificial intelligence processes and then performing altering the 3D volumetric dataset. Step 2400 is to generate a 3D dataset via AI processes, such as is performed in U.S. patent application Ser. No. 16/703,629. Step 2401 is to assign at least one mechanical type property (e.g., tissue type property) to the 3D volumetric dataset. Step 2402 is to perform rendering of the 3D volumetric dataset wherein the 3D volumetric dataset has a first configuration. Step 2403 is to receive an input to cause the 3D volumetric dataset to change to a subsequent configuration wherein the change to a subsequent configuration is in accordance with the nature of the input and the mechanical type properties of the 3D dataset. Step 2404 is to change the 3D volumetric dataset to the subsequent configuration (e.g., through voxel manipulation). Step 2405 is to perform rendering of the 3D volumetric dataset in the subsequent configuration.

What is claimed is:

1. A method of altering an imaging examination comprising:
  using a three-dimensional dataset of a portion of a physical item,
    wherein said three-dimensional dataset is comprised of voxels, and
    wherein said voxels in said three-dimensional dataset have numerical values;
  modifying voxels of said three-dimensional dataset to generate a simulated change of said physical item comprising:
    wherein said modifying voxels of said three-dimensional dataset comprises altering numerical values of voxels corresponding to said physical item of said three-dimensional dataset,
    wherein said altering said numerical values of voxels corresponding to said physical item of said three-dimensional dataset is performed in accordance with said simulated change of said physical item,
    wherein said modifying voxels of said three-dimensional dataset creates a modified three-dimensional dataset, and
    wherein said modified three-dimensional dataset comprises said simulated change; and
  displaying said modified three-dimensional dataset to a user.

2. The method of claim 1 further comprising performing additional modifications of numerical values of voxels of said modified three-dimensional dataset to generate a second modified three-dimensional dataset wherein said second modified three-dimensional dataset simulates a different time point.

3. The method of claim 2 wherein at said different time point, an additional change occurs.

4. The method of claim 1 further comprising wherein said change comprises alterations to said physical item's structure.

5. The method of claim 1 further comprising wherein said change is performed in response to a geo-registered tool.

6. The method of claim 1 further comprising wherein said change is performed in response to a virtual tools.

7. The method of claim 1 further comprising wherein said change is performed in response to a dissection.

8. The method of claim 1 further comprising wherein said change comprises changes over time due to age.

9. The method of claim 1 further comprising wherein said change comprises pathology.

10. The method of claim 1 further comprising creating new voxels corresponding to said simulated change of said physical item.

11. The method of claim 1 further comprising eliminating voxels corresponding to said simulated change of said physical item.

12. The method of claim 1 further comprising wherein said simulated change of said physical item is based on a mechanical property of said physical item comprising elasticity, ductility or hardness.

13. The method of claim 1 further comprising wherein said simulated change of said physical item is based on a physical property of said physical item comprising density or thermal conductivity.

14. The method of claim 1 further comprising wherein a set of voxels is transferred to a virtual bucket for analysis.

15. The method of claim 1 further comprising wherein said simulated change of said physical item is in accordance with a strategic deformation point.

16. The method of claim 1 further comprising wherein said simulated change of said physical item is performed by an artificial intelligence algorithm.

17. The method of claim 1 further comprising wherein said simulated change of said physical item comprises changing said physical item's position and an orientation.

18. The method of claim 1 further comprising wherein said simulated change of said physical item comprises changing said physical item's shape and size.

19. A non-transitory computer readable medium having computer readable code thereon, the medium comprising instructions for altering an imaging examination comprising:
  using a three-dimensional dataset of a portion of a physical item,
    wherein said three-dimensional dataset is comprised of voxels, and
    wherein said voxels in said three-dimensional dataset have numerical values;

modifying voxels of said three-dimensional dataset to generate a simulated change of said physical item comprising:
- wherein said modifying voxels of said three-dimensional dataset comprises altering numerical values of voxels corresponding to said physical item of said three-dimensional dataset,
- wherein said altering said numerical values of voxels corresponding to said physical item of said three-dimensional dataset is performed in accordance with said simulated change of said physical item,
- wherein said modifying voxels of said three-dimensional dataset creates a modified three-dimensional dataset, and
- wherein said modified three-dimensional dataset comprises said simulated change; and displaying said modified three-dimensional dataset to a user.

20. A computer system comprising:
a memory;
a processor;
a communications interface;
an interconnection mechanism coupling the memory, the processor and the communications interface; and
wherein the memory is encoded with an application, that when performed on the processor, provides a process for simulating physiology in an imaging examination, the process causing the computer system to perform the operations of:

using a three-dimensional dataset of a portion of a physical item,
- wherein said three-dimensional dataset is comprised of voxels, and
- wherein said voxels in said three-dimensional dataset have numerical values;

modifying voxels of said three-dimensional dataset to generate a simulated change of said physical item comprising:
- wherein said modifying voxels of said three-dimensional dataset comprises altering numerical values of voxels corresponding to said physical item of said three-dimensional dataset,
- wherein said altering said numerical values of voxels corresponding to said physical item of said three-dimensional dataset is performed in accordance with said simulated change of said physical item,
- wherein said modifying voxels of said three-dimensional dataset creates a modified three-dimensional dataset, and
- wherein said modified three-dimensional dataset comprises said simulated change; and displaying said modified three-dimensional dataset to a user.

* * * * *